US011254678B2

(12) United States Patent
Liu et al.

(10) Patent No.: US 11,254,678 B2
(45) Date of Patent: Feb. 22, 2022

(54) MIXED-VALENCE CRYSTAL SUPERSTRUCTURES

(71) Applicants: Northwestern University, Evanston, IL (US); King Abdulaziz City for Science and Technology (KACST), Riyadh (SA)

(72) Inventors: Zhichang Liu, Hangzhou (CN); James Fraser Stoddart, Evanston, IL (US)

(73) Assignees: Northwestern University, Evanston, IL (US); King Abdulaziz City for Science and Technology (KACST), Riyadh (SA)

(*) Notice: Subject to any disclaimer, the term of this patent is extended or adjusted under 35 U.S.C. 154(b) by 0 days.

(21) Appl. No.: 16/972,110

(22) PCT Filed: Jun. 4, 2019

(86) PCT No.: PCT/US2019/035399
§ 371 (c)(1),
(2) Date: Dec. 4, 2020

(87) PCT Pub. No.: WO2019/236587
PCT Pub. Date: Dec. 12, 2019

(65) Prior Publication Data
US 2021/0221811 A1    Jul. 22, 2021

Related U.S. Application Data

(60) Provisional application No. 62/680,352, filed on Jun. 4, 2018.

(51) Int. Cl.
*C07D 471/22* (2006.01)
*C07D 213/22* (2006.01)
*C30B 7/14* (2006.01)
*C30B 29/54* (2006.01)

(52) U.S. Cl.
CPC ......... *C07D 471/22* (2013.01); *C07D 213/22* (2013.01); *C30B 7/14* (2013.01); *C30B 29/54* (2013.01); *C07B 2200/13* (2013.01)

(58) Field of Classification Search
None
See application file for complete search history.

(56) References Cited

U.S. PATENT DOCUMENTS 9,120,799 B2    9/2015    Fahrenbach

OTHER PUBLICATIONS

Ashton, P. R., et al. "Diazapyrenium-containing catenanes and rotaxanes." New Journal of Chemistry 23.6 (1999): 587-602.

Berville, M., et al. "Viologen cyclophanes: redox controlled host-guest interactions." Chemical Communications 51.87 (2015): 15772-15775.

Bockman, T. M., et al. "Isolation and oxidation-reduction of methylviologen cation radicals. Novel disproportionation in charge-transfer salts by X-ray crystallography." The Journal of Organic Chemistry 55.13 (1990): 4127-4135.

Fahrenbach, A. C., et al. "Solution-phase mechanistic study and solid-state structure of a tris (bipyridinium radical cation) inclusion complex." Journal of the American Chemical Society 134.6 (2012): 3061-3072.

Frasconi, M., et al. "Redox control of the binding modes of an organic receptor." Journal of the American Chemical Society 137.34 (2015): 11057-11068.

Geraskina, M. R., et al. "The Viologen Cation Radical Pimer: A Case of Dispersion-Driven Bonding." Angewandte Chemie International Edition 56.32 (2017): 9435-9439.

Hankache, J., et al. "Organic mixed valence." Chemical reviews 111.8 (2011): 5138-5178.

International Searching Authority. International Search Report and Written Opinion for application PCT/US2019/035399. dated Sep. 19, 2019. 9 pages.

Ivanov, M. V., et al. "From Intramolecular (Circular) in an Isolated Molecule to Intermolecular Hole Delocalization in a Two-Dimensional Solid-State Assembly: The Case of Pillarene." Angewandte Chemie International Edition 57.8 (2018): 2144-2149.

Jankowski, C. K., et al. "Factors Affecting the Formation of 2: 1 Host: Guest Inclusion Complexes of 2-[(R-Phenyl)amine]-1, 4-naphthalenediones (PAN) in β-and ?-Cyclodextrins." Molecules 21.11 (2016): 1568.

Ko, Y. H., et al. "Supramolecular assemblies built with host-stabilized charge-transfer interactions." Chemical communications 13 (2007): 1305-1315.

Leblanc, N., et al. "Unprecedented stacking of MV 2+ dications and MV?+ radical cations in the mixed-valence viologen salt (MV) 2 (BF 4) 3 (MV= methylviologen)." Chemical Communications 49.87 (2013): 10272-10274.

Li, H., et al. "Mechanical bond-induced radical stabilization." Journal of the American Chemical Society 135.1 (2013) 456-467.

Lindeman, S. V., et al. "X-ray structure analysis and the intervalent electron transfer in organic mixed-valence crystals with bridged aromatic cation radicals." Journal of the American Chemical Society 124.5 (2002): 843-855.

Liu, Z., et al. "Mixed-Valence Superstructure Assembled from a Mixed-Valence Host-Guest Complex." Journal of the American Chemical Society 140.30 (Jun. 27, 2018): 9387-9391.

McDermott, G. M., et al. "Crystal structure of an integral membrane light-harvesting complex from photosynthetic bacteria." Nature 374.6522 (1995): 517-521.

Murase, T. et al. "Pairwise selective formation of aromatic stacks in a coordination cage." Journal of the American Chemical Society 132.23 (2010): 7864-7865.

(Continued)

*Primary Examiner* — Samantha L Shterengarts
(74) *Attorney, Agent, or Firm* — Quarles & Brady LLP

(57) ABSTRACT

Disclosed herein is a mixed-valence crystal superstructure assembled from a 2:1 host-guest inclusion complex. The complex comprises an aromatic guest encircled by two macrocycles, wherein the complex has an empirical charge greater than 0 and less than 1. Methods of preparing the compositions described herein are also disclosed.

20 Claims, 11 Drawing Sheets

(56) References Cited

OTHER PUBLICATIONS

Odell, B., et al. "Cyclobis (paraquat-p-phenylene). A Tetracationic Multipurpose Receptor." Angewandte Chemie International Edition in English 27.11 (1988): 1547-1550.
Porter, W. W., et al. "Synthesis and Characterization of a Highly Reducing Neutral "Extended Viologen" and the Isostructural Hydrocarbon 4, 4-Di-n-octyl-p-quaterphenyl." Journal of the American Chemical Society 127.47 (2005): 16559-16566.
Sun, J., et al. "Mechanical-bond-protected, air-stable radicals." Journal of the American Chemical Society 139.36 (2017): 12704-12709.
Trabolsi, A., et al. "Radically enhanced molecular recognition." Nature chemistry 2.1 (2010): 42.
Winkler, J. R., et al. "Long-range electron tunneling." Journal of the American Chemical Society 136.8 (2014) 2930-2939.
Yoshizawa, M. et al. "Room-temperature and solution-state observation of the mixed-valence cation radical dimer of tetrathiafulvalene,[(TTF) 2]+•, within a self-assembled cage." Journal of the American Chemical Society 127.39 (2005): 13456-13457.
Zhu, W., et al. "Revealing the charge-transfer interactions in self-assembled organic cocrystals: two-dimensional photonic applications." Angewandte Chemie (International ed. in English) 54.23 (2015): 6785.

Fig. 4I
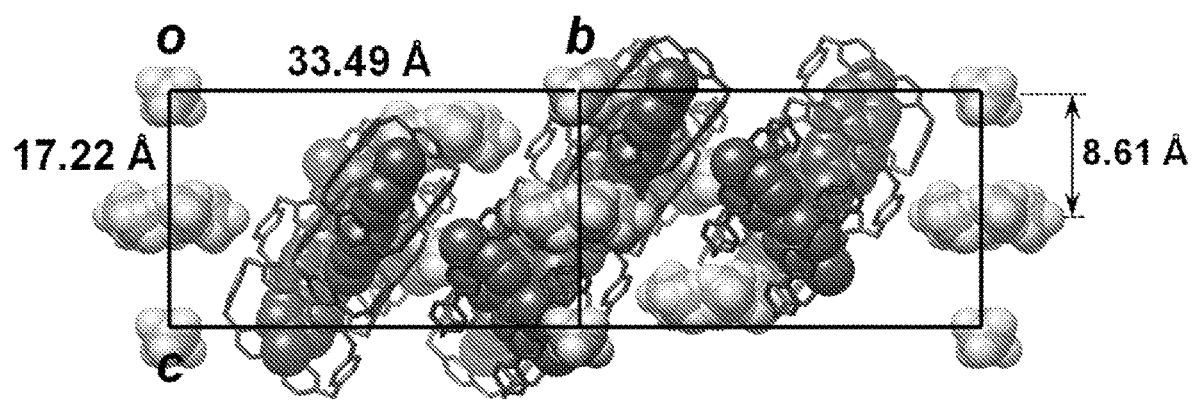
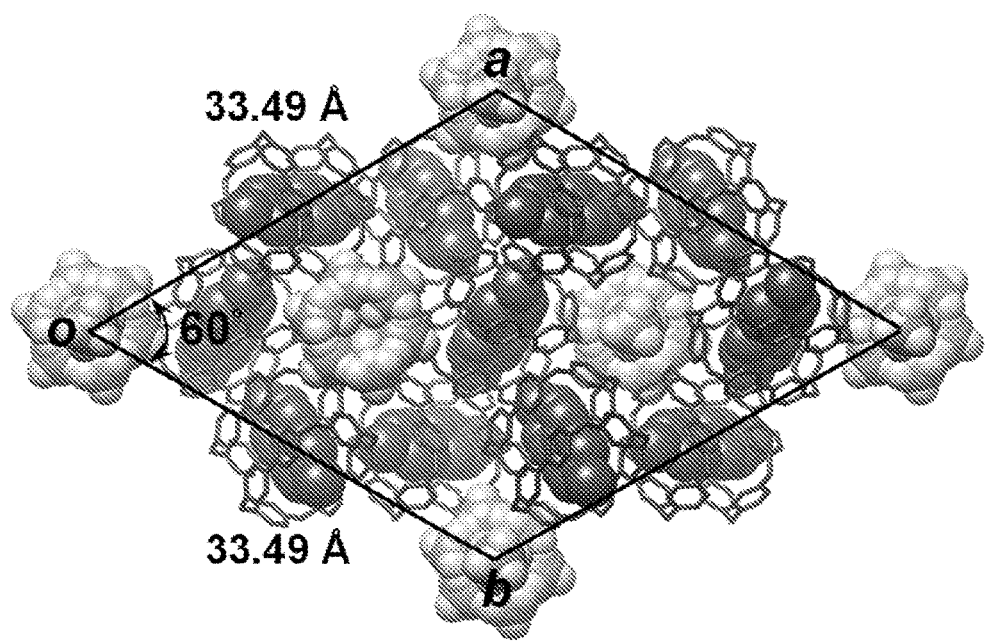
Fig. 4K

MIXED-VALENCE CRYSTAL SUPERSTRUCTURES

CROSS-REFERENCE TO RELATED APPLICATIONS

This application represent the U.S. nation stage entry of International Application PCT/US2019/035399 filed Jun. 4, 2019, which claims benefit of priority of U.S. Patent Application Ser. No. 62/680,352, filed Jun. 4, 2018, the contents of each are incorporated herein by reference in their entireties.

BACKGROUND

Cyclobis(paraquat-p-phenylene) ($CBPQT^{4+}$) ring, which is composed of two 1,1'-dialkyl-4,4'-bipyridinium ($BIPY^{2+}$) dicationic units held rigidly, is capable of forming inclusion complexes with a wide range of neutral π-electron-rich guests through π-π stacking and charge-transfer (CT) interactions. $CBPQT^{4+}$, when reduced to its diradical dicationic $CBPQT^{2(\cdot+)}$, forms a stable 1:1 trisradical tricationic inclusion complex $BIPY^{\cdot+} \subset CBPQT^{2(\cdot+)}$ with appropriate guests containing $BIPY^{\cdot+}$ units on account of favorable radical-radical interactions. By employing this 1:1 inclusion complex as a template motif, a number of high energy mechanically interlocked molecules (MIMs) have been prepared. All of these MIMs exhibit intramolecular electron delocalization properties between their BIPY units in their mixed-valence states thanks to the protection provided by the mechanic bond. However, there exists a need for that precise tuning of the redox states in host-guest systems for achieving long-range electron delocalization in solid-state devices such as data memories, superconductors, and optoelectronic devices.

BRIEF SUMMARY OF THE INVENTION

Disclosed herein is an unprecedented mixed-valence in a crystal superstructure assembled from a unique 2:1 host-guest inclusion complex. One aspect of the invention provides for a mixed-valence host-guest inclusion complex comprising an aromatic guest encircled by two macrocycles, wherein the complex has an empirical charge greater than 0 and less than 1. The aromatic guest may comprise a compound of Formula I

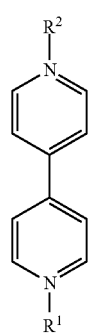

(I)

where $R^1$ and $R^2$ are each independently selected from alkyl, cycloalkyl, heterocycloalkyl, aryl, heteroaryl, alkenyl, alkynyl, alkyleneazido, alkylenecycloalkyl, alkyleneheterocycloalkyl, or alkylenearyl. In some embodiments, the aromatic guest comprises methyl viologen. In some embodiments, at least one of the two macrocycles encircling the aromatic guest comprise cyclobis(paraquat-p-phenylene). In particular embodiments, each of the two macrocycles encircling the aromatic guest comprise cyclobis(paraquat-p-phenylene). In a particular embodiment, the complex has an empirical formula of $[MV \subset (CBPQT)_2]^{2/3+}$.

Another aspect of the invention provides for a mixed-valence superstructure. The mixed-valence superstructure may comprise an ordered arrangement of a multiplicity of any of the complexes described herein. The superstructure may further comprise a counter anion. In some embodiments, the superstructure comprises an octahedral arrangement of the multiplicity of complexes. Examples of counter anions include $PF_6^-$. In particular embodiments, the superstructure has an empirical formula of $[MV \subset (CBPQT)_2]_3 \cdot (PF_6)_2$.

Another aspect of the invention provides for a crystalline composition. The crystalline composition may comprise an ordered arrangement of a plurality of any of the complexes or superstructures described herein. In some embodiments, the composition comprises a body-centered cubic arrangement of the plurality of superstructures. In some embodiments, the ordered arrangement results in channels running through the composition. In certain embodiments, composition further comprises a counter anion disposed within the channels. In certain embodiments, the composition has an empirical formula of $[MV \subset (CBPQT)_2]_3 \cdot (PF_6)_2$. In certain embodiments, the composition has a molecular packing arrangement defined by space group $R\bar{3}$. In certain embodiments, the composition has a molecular packing arrangement defined by unit cell dimensions a=33.5±0.1, b=33.5±0.1, c=17.2±0.1, α=90°, β=90°, and γ=120°.

Another aspect of the invention provides for a method for the preparation of a mixed-valence host-guest complexes. The method may comprise contacting a mixture comprising an aromatic guest and a macrocycle with a reducing agent, wherein the mixed-valence host guest complex comprises an aromatic guest encircled by two macrocycles.

Another aspect of the invention provides for a method for the preparation of crystalline compositions. The method may comprise contacting a mixture comprising an aromatic guest and a macrocycle with a reducing agent to prepare a plurality of mixed-valence host guest complexes and crystallizing the plurality of complexes to prepare the crystalline composition, wherein the mixed-valence host guest complex comprises an aromatic guest encircled by two macrocycles and wherein the crystalline composition comprises an ordered arrangement of a plurality of complexes.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 2A shows a front view showing the corner angles of CBPQT rings, torsional angle of BIPY in CBPQT, and [C—H . . . π] interactions (dash lines). FIG. 2B shows a side view exhibiting the angles between xylene planes and CBPQT ring and the dihedral angle between MV and CBPQT as well as [H . . . H] interactions (dash lines) between two CBPQT rings. FIG. 2C shows a top view indicating the $C_2$ symmetrical axis of the complex and the width of CBPQT as well as [π . . . π] interaction distance between MV and CBPQT.

FIG. 4A shows a octahedron assembled from six $MV \subset (CBPQT)_2$ units surrounding two $PF_6^-$ anions and FIG. 4E is a schematic representation of FIG. 4A. FIG. 4B shows a body-centered cubic superstructure assembled by adjacent octahedrons sharing $MV \subset (CBPQT)_2$ as linkers and FIG. 4F is a schematic representation of FIG. 4B. FIG. 4C shows a hexagonal arrangement as viewed along c-axis along the diagonal of the cube in FIG. 4B. FIG. 4D shows hexagonal channels filled with $PF_6^-$ anions spaced 8.61 Å apart from each other. FIG. 4G shows a representation where every $MV \subset (CBPQT)_2$ is encircled by four $MV \subset (CBPQT)_2$ units in the equatorial plane and two pairs of $PF_6^-$ anions at two vertices. FIG. 4H shows 20 Complementary [C—H . . . π] interactions ranging from 2.59-2.79 Å between BIPY planes and the H atoms on CBPQT rings of adjacent five $MV \subset (CBPQT)_2$ units. Solvent molecules for the sake of clarity. The six $PF_6^-$ symmetry-equivalent positions with ⅙ occupancy at each position are represented by a cluster of six $PF_6^-$.

FIGS. 4I-4K show three views of the single-crystal X-ray superstructure of the complex $[MV \subset (CBPQT)_2]_3 \cdot (PF_6)_2$. FIG. 4I shows a front view, FIG. 4J shows a side view, and FIG. 4K shows a top view. When viewing down along the c crystallographic axis, hexagonal channels are filled with $PF_6^-$ anions spaced 8.61 Å apart from each other can be observed to pack into trigonal arrangements. One of the $PF_6$ anion pairs is disordered about a 6-fold crystallographic c-axis. CBPQT is depicted as tubular representation, while MV, and $PF_6^-$ are depicted as space-filling representations. Hydrogen atoms and solvent molecules are omitted for the sake of clarity. The six $PF_6^-$ symmetry-equivalent positions with ⅙ occupancy at each position are represented by a cluster of six $PF_6^-$.

DETAILED DESCRIPTION OF THE INVENTION

Figure 1A:
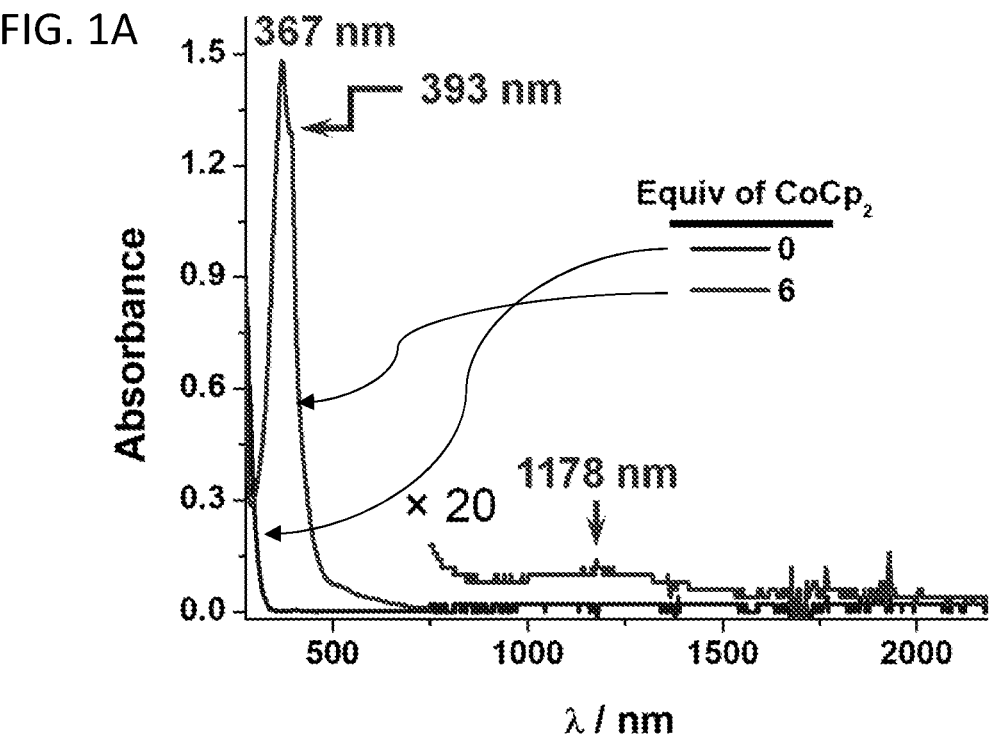
FIGS. 1A-1B show the UV-Vis-NIR Absorption (FIG. 1A) and EPR spectra (FIG. 1B) of an equimolar mixture of $CBPQT \cdot 4PF_6$ (0.08 mM) and $MV \cdot 2PF_6$ (0.08 mM) and its reduced product upon addition of 6 equiv of $CoCp_2$. All spectra were recorded in Ar-purged MeCN solutions at 298 K.
Figure 1B:
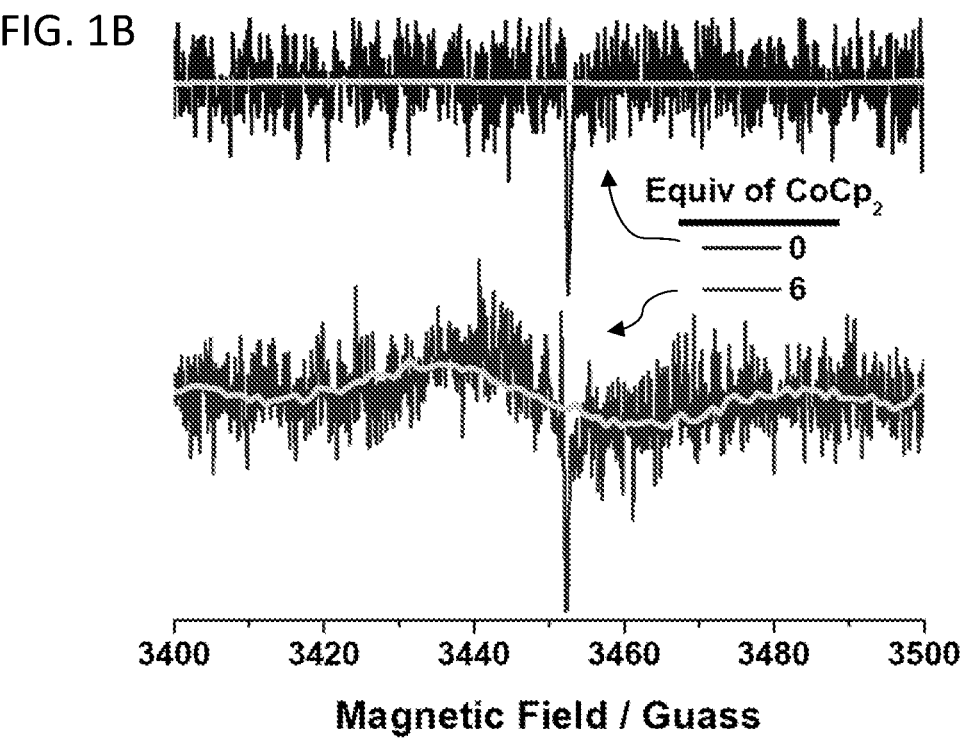

Herein we demonstrate an unprecedented example of mixed-valence in a crystal superstructure assembled from a unique 2:1 host-guest inclusion complex. The 2:1 host-guest inclusion complex comprises an aromatic guest encircled by two aromatic macrocycles. Remarkably, the complex bears evenly a non-integer positive charge between 0 and 1 and the positive charges is distributed statistically among a multiplicity of complexes. The formation of the mixed-valence complex allows for the formation of an ordered arrangement of a multiplicity of complexes and the preparation of crystalline compositions. Our findings demonstrate precise tuning of the redox states in host-guest systems, leading to a supramolecular strategy for achieving long-range electron delocalization in solid-state devices such as data memories, superconductors, and optoelectronic devices.

Provided herein are mixed-valence host-guest inclusion complexes. A "host-guest inclusion complex" (or "complex") is a complex in which one component (the host) forms a cavity in which molecular entities of a second chemical species (the guest) are located. There is no covalent bonding between guest and host, the attraction being generally due to non-covalent interactions such as π-π stacking, charge-transfer interactions, radical-radical interactions, van der Waals forces, and the like. The host-guest inclusion complex may be denoted "guest⊂host", e.g., $MV \subset (CBPQT)_2$ where a MV guest is hosted by two CBPQT hosts.

Also provided herein are superstructures comprising a multiplicity of host-guest inclusion complexes. A "superstructure" is an ordered arrangement of components on a length scale larger than that of the individual components. The host-guest inclusion complexes form an ordered arrangement of complexes. Suitably the superstructure is an octahedral arrangement of complexes. When the ordered arrangement is described by a geometric term, such as octahedral, the geometric term allows for some variance in the positioning of the complexes so long as the ordered arrangement is reasonably described by the geometric term. For example, the use of the term "octahedral" allows for arrangements having a generally octahedral arrangement. The complexes may self-assemble into the organized superstructure as a consequence of specific, local interactions between the components themselves. The superstructure may comprise, in addition to a multiplicity of complexes, a second component. The second component may be a counter ion such as an anion like $PF_6^-$.

Also provided herein are crystalline compositions. "Crystalline compositions" are solid materials whose constituents, such as hosts, guests, counter ions, complexes, or superstructures, are arranged in an ordered structure forming a crystal lattice extending in all directions. The crystalline composition may be formed from an ordered arrangement of superstructures or the complexes. Suitably, the crystalline composition is formed from a body-centered cubic arrangement of superstructures. When the ordered arrangement is described by a geometric term, such as body-centered cubic, the geometric term allows for some variance in the positioning of the complexes so long as the ordered arrangement is reasonably described by the geometric term. For example, the use of the term "body-centered cubic" allows for arrangements having a generally body-centered cubic arrangement.

As used herein, "mixed-valence" means that a compound has an atom present in more than one oxidation state. Suitably, mixed valency is the result of the distribution of a delocalized electron across two or more compounds or complexes. Mixed-valence compounds may have a non-integer empirical charge q, such as a 0<q<1 or q=⅔. The distribution of the delocalized electron may be over the host compounds of the complex, the guest compounds of the complex, or both the host and guest compounds of the complex. In some cases the distribution of the delocalized electron may be over two or more inclusion complexes. As shown in the Examples that follow, one MV encircled by two CBPQT macrocycles (MV⊂(CBPQT)$_2$) may bear evenly an empirical ⅔ positive charge. As a result, an electron may be distributed statistically among a total number of 15 BIPY units assembled into three MV⊂(CBPQT)$_2$ complexes. In other words, one electron may be distributed over 15 BIPY units composed of three [MV⊂(CBPQT)$_2$]$^{·+}$ complexes, giving an unparalleled ratio of 15:2 of BIPY/charge.

The complex comprises an aromatic guest molecule that is encircled by two aromatic host macrocycles. The aromatic guest may suitably be any aromatic molecule that is capable of forming a 2:1 inclusion complex with the two aromatic macrocycles. In some embodiments, the guest is a viologen. As used herein a viologen is an organic compound comprising a bipyridinium (BIPY) subunit such as compounds of the general formula $(C_5H_4NR)_2^{2+}$. Viologens may adopt a number of different electronic states such as cationic (e.g., 2+), neutral (0), radical-cationic (e.g., ·+), or mixed-valence states having non-integer empirical charges. Exemplary viologens comprise compounds of Formula I

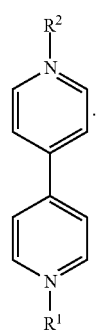

(I)

For the purposes of generality, the compound of Formula I is not assigned a particular electronic state for all purposes, e.g., cationic, neutral, radical-cationic, or mixed-valence, but one may be assigned depending on the context. The radicals R$^1$ and R$^2$ are each independently selected from alkyl, cycloalkyl, heterocycloalkyl, aryl, heteroaryl, alkenyl, alkynyl, alkyleneazido, alkylenecycloalkyl, alkyleneheterocycloalkyl, or alkylenearyl. Each R$^1$ and R$^2$ can be the same or different. Choice of steric and electronic properties of the R groups can influence the end properties of the complex. For example, the complex can be tuned by these selections to provide a complex with a particular conductance, redox potential, and/or UV-vis property. Exemplary guests suitable for use with the complexes described herein and methods for preparing the guests have previously described in U.S. Pat. No. 9,120,799, issued Sep. 1, 2015, to Fahrenbach et al., the contents of which is incorporated herein in its entirety.

Some specific R groups for the compound of formula (I) may include, without limitation,

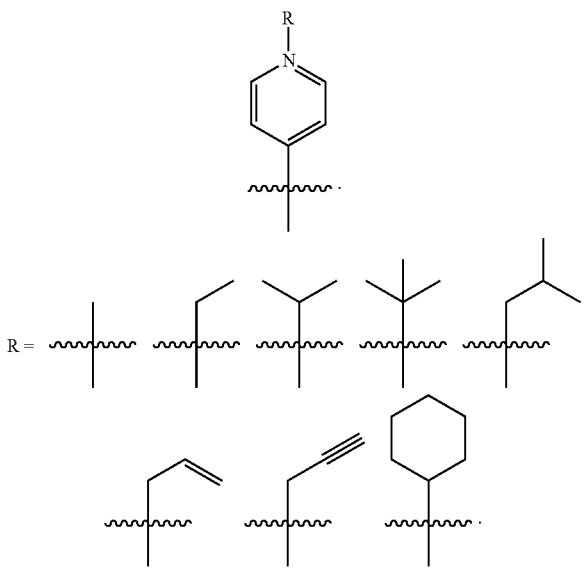

These are but only a few representative examples of the possible alkyl groups. Other examples include where the above functional groups have been modified by halogens in some position(s), with hydroxyl groups, with carboxylates, with esters, with amines, with amides, with azides, and with ethers. The limitation to the alkyl-based substitution occurs when the alkyl chains becomes so long that the large degree of freedom associated with rotation about the sp$^3$ C—C bonds prevents efficient crystallization from occurring.

Possible aryl substituents to the 4,4' positions of bipyridine are shown below and include phenyl, naphthyl, and pyrenyl derivatives.

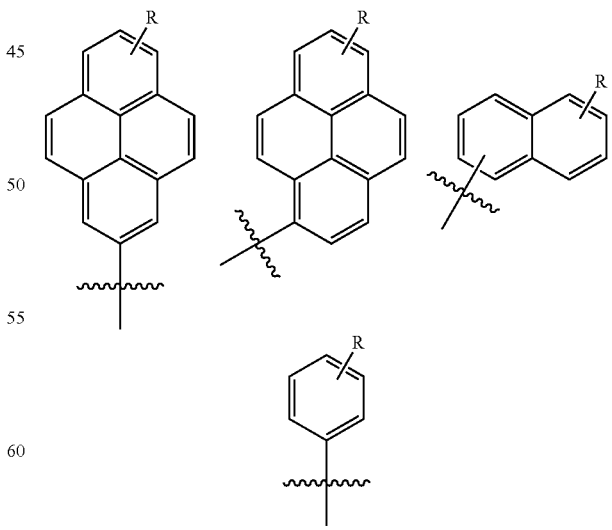

Upon these aryl substituents, additional functional groups of either electron-donating or electron-withdrawing natures may be covalently attached. These functional groups are shown below, and more than one or different combinations of them may be imposed on the aryl substituents.

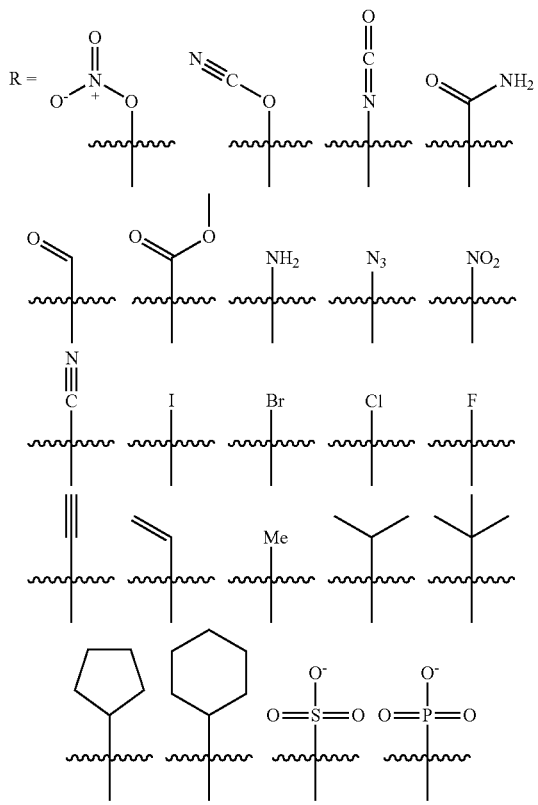

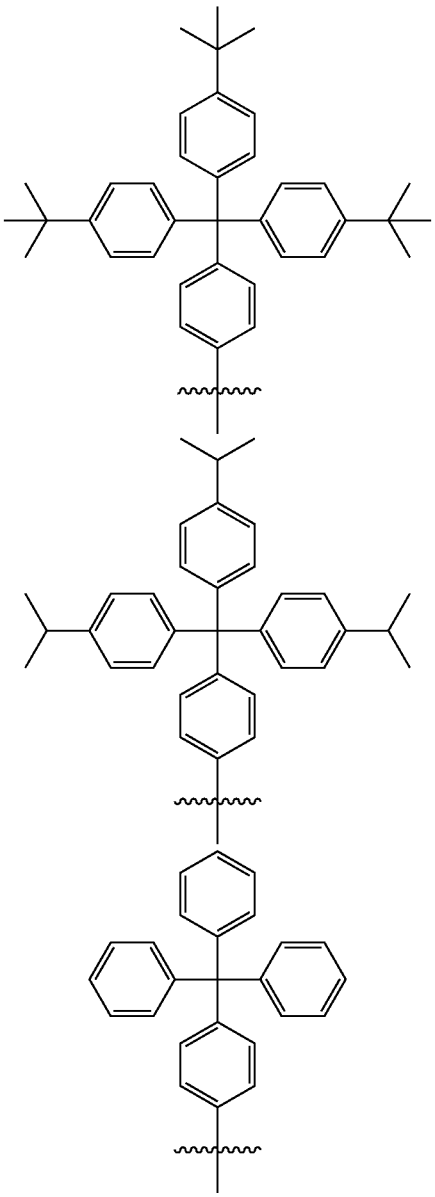

The limitation to this functionalization occurs when the resulting dimensions of the functionalized aryl-substituent becomes sterically too large such that threading of the aromatic macrocycles can no longer occur.

In consideration that the approximate dimensions of a CBPQT ring are approximately 10 Å×7 Å, the following functionalized aryl substituents represent the limit of steric bulk imposed such that anything sterically larger will prevent the CBPQT from threading.

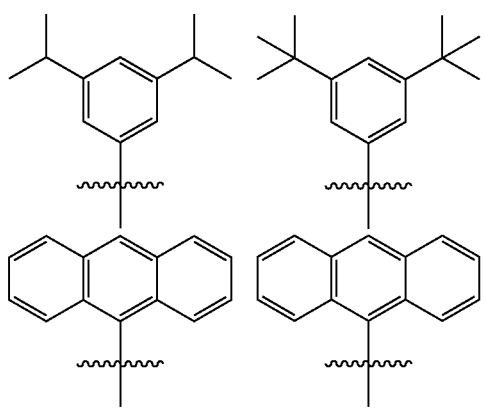

The following are examples of functionalized aryl substituents which are above the steric limit for threading of a CBPQT to occur.

In these specific cases, a clipping mechanism must be pursued rather than a threading mechanism in order to see the CBPQT encircled around the central BIPY core.

The term "alkyl" used herein refers to a saturated or unsaturated straight or branched chain hydrocarbon group of one to forty carbon atoms, including, but not limited to, methyl, ethyl, n-propyl, isopropyl, n-butyl, isobutyl, tert-butyl, n-hexyl, and the like. Alkyls of one to six carbon atoms are also contemplated. The term "alkyl" includes "bridged alkyl," i.e., a bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups optionally can be substituted, for example, with hydroxy (OH), halide, thiol (SH), aryl, heteroaryl, cycloalkyl, heterocycloalkyl, and amino. It is specifically contemplated that in the compounds described herein the alkyl group consists of 1-40 carbon atoms, preferably 1-25 carbon atoms, preferably 1-15 carbon atoms, preferably 1-12 carbon atoms, preferably 1-10 carbon atoms, preferably 1-8 carbon atoms, and preferably 1-6 carbon atoms. "Heteroalkyl" is defined similarly as alkyl, except the heteroalkyl contains at least one heteroatom independently selected from the group consisting of oxygen, nitrogen, and sulfur.

As used herein, the term "cycloalkyl" refers to a cyclic hydrocarbon group, e.g., cyclopropyl, cyclobutyl, cyclohexyl, and cyclopentyl. "Heterocycloalkyl" is defined similarly as cycloalkyl, except the ring contains one to three heteroatoms independently selected from the group consisting of oxygen, nitrogen, and sulfur. Nonlimiting examples of heterocycloalkyl groups include piperdine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected from the group consisting of alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

The term "alkenyl" used herein refers to a straight or branched chain hydrocarbon group of two to ten carbon atoms containing at least one carbon double bond including, but not limited to, 1-propenyl, 2-propenyl, 2-methyl-1-propenyl, 1-butenyl, 2-butenyl, and the like. The term "cycloalkenyl" refers to a cycloalkyl group having one or more double bonds. "Heterocycloalkenyl" refers to a cycloalkenyl group having one or more heteroatoms (e.g., N, S, O, or combinations thereof).

The term "alkynyl" used herein refers to a straight or branched chain hydrocarbon group of two to ten carbon atoms containing at least one carbon triple bond including, but not limited to, 1-propynyl, 2-propynyl, 1-butynyl, 2-butynyl, and the like.

The term "halide" or "halo" used herein refers to fluoro, chloro, bromo, or iodo.

The term "alkylene" used herein refers to an alkyl group having a substituent. For example, the term "alkylene aryl" refers to an alkyl group substituted with an aryl group. The alkylene group is optionally substituted with one or more substituent previously listed as an optional alkyl substituent. For example, an alkylene group can be —CH$_2$CH$_2$— or —CH$_2$—.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, OCF$_3$, NO$_2$, CN, NC, OH, alkoxy, amino, CO$_2$H, CO$_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "alkoxy" used herein refers to straight or branched chain alkyl group covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "thioalkyl" used herein refers to one or more thio groups appended to an alkyl group.

The term "thioether" used herein refers to straight or branched chain alkyl or cycloalkyl group covalently bonded to the parent molecule through an —S— linkage. Examples of thioether groups include, but are not limited to, —SCH$_3$, —SCH$_2$CH$_3$, —SCH$_2$CH$_2$CH$_3$, —SCH(CH$_3$)$_2$, —SCH$_2$CH$_2$CH$_2$CH$_3$, —SCH$_2$CH(CH$_3$)$_2$, —SC(CH$_3$)$_3$ and the like.

The term "hydroxyalkyl" used herein refers to one or more hydroxy groups appended to an alkyl group.

The term "azide" refers to a —N$_3$ group. The term "nitro" refers to a —NO$_2$ group.

The term "amino" as used herein refers to —NR$_2$, where R is independently hydrogen, optionally substituted alkyl, optionally substituted heteroalkyl, optionally substituted cycloalkyl, optionally substituted heterocycloalkyl, optionally substituted aryl or optionally substituted heteroaryl. Non-limiting examples of amino groups include NH$_2$, NH(CH$_3$), and N(CH$_3$)$_2$. In some cases, R is independently hydrogen or alkyl.

The term "amido" as used herein refers to —C(O)NH$_2$, —C(O)NR$_2$, —NRC(O)R or —NHC(O)H, where each R is independently hydrogen, optionally substituted alkyl, optionally substituted heteroalkyl, optionally substituted cycloalkyl, optionally substituted heterocycloalkyl, optionally substituted aryl or optionally substituted heteroaryl. In some cases, the amido group is —NHC(O)alkyl or —NHC(O)H. In various cases, the amido group is —C(O)NH(alkyl) or —C(O)NH(substituted alkyl). A non-limiting example of an amido group is —NHC(O)CH$_3$.

As used herein, a substituted group is derived from the unsubstituted parent structure in which there has been an exchange of one or more hydrogen atoms for another atom or group. A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (B) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from:
   (i) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and
   (ii) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected:

(a) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (b) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl.

The term "carboxy" or "carboxyl" used herein refers to —COOH or its deprotonated form —COO$^-$. $C_{1-10}$carboxy refers to optionally substituted alkyl or alkenyl groups having a carboxy moiety. Examples include, but are not limited to, —CH$_2$COOH, —CH$_2$CH(COOH)CH$_3$, and —CH$_2$CH$_2$CH$_2$COOH.

In some cases, the substituent group(s) is (are) one or more group(s) individually and independently selected from alkyl, cycloalkyl, aryl, heterocyclyl, heteroaryl, hydroxy, alkoxy, aryloxy, mercapto, alkylthio, arylthio, cyano, halo, carbonyl, thiocarbonyl, alkoxycarbonyl, nitro, silyl, trihalomethanesulfonyl, trifluoromethyl, and amino, including mono and di substituted amino groups, and the protected derivatives thereof.

The aromatic macrocycle may be any host ring compound capable of forming a 2:1 host-guest inclusion complex with the guest compound. As such the macrocycle must be large enough to allow for the guest to the threaded into the macrocycle but should preferably allow for stabilizing π-π stacking, charge-transfer interactions, and/or van der Waals interactions between the host macrocycle and the guest. The macrocycle may comprise one or more BIPY subunits such as CBPQT. As with the viologens described above, macrocycles comprising one or more BIPY subunits may adopt a number of different electronic states, including cationic (e.g., 4+), neutral (0), radical-cationic (e.g., 2(·+) or (2+)(·+)), or mixed-valence states having non-integer charges. For the purposes of generality, the macrocycle or CBQPT is not assigned a particular electronic state for all purposes, e.g., cationic, neutral, radical-cationic, or mixed-valence, but one may be assigned depending on the context.

These complexes can be isolated as crystalline compositions, e.g., a single crystal. The crystalline composition are prepared following the formation of the host-guest complex. This in turn, allows for creation of a large variety of materials by inserting different guests, with different electronic properties into the host. In this way the electronic properties of the material can be tuned in a modular way.

The complexes may be prepared by contacting a mixture comprising the aromatic guest and macrocycle with a reducing agent. The molar ratio of hosts to guests may vary, leading to an excess of one or the other. The mixture may have any suitable molar ratio of hosts to guests such as between a 2.0:1.0 and 1.0:2.0 molar ratio of aromatic guest to macrocycle, including between 1.8:1.0 and 1.0:1.8, 1.6:1.0 and 1.0:1.6, 1:4:1.0 and 1.0:1.4, or 1.2:1.0 and 1.2:1.0. In the Examples, the mixture is an equimolar mixture of aromatic guest to macrocycle is used.

Suitably the reducing agent is capable of reducing cationic or radical-cationic guests and/or macrocyclic hosts such that the majority of the guests or hosts are in a neutral state. Reducing agents suitable for this purpose include colbaltocene (CoCp$_2$). The number of reducing agent equivalents to the contacted with the mixture of aromatic guests and macrocycles may be selected based on the number of guests, the number of hosts, or a combination thereof. For example, the mixture of hosts and guests may be contacted with between 2 and 10 equivalents of the reducing agent, including between 3 and 9 equivalents, between 4 and 8 equivalents, between 5 and 7 equivalents, or approximately 6 equivalents. Suitably, an equimolar mixture of hosts and guests may be contacted with 6 equivalents of reducing agents.

The method may be performed in any suitable solvent that allows for complex formation. Suitably the solvent may be selected from a nitrile, such as CH$_3$CN, a alkyl halide, such as CH$_2$Cl$_2$, or a combination thereof, e.g., a CH$_3$CN/CH$_2$Cl$_2$ solution.

Crystalline compositions having an ordered arrangement of a plurality of complexes may be prepared Many methods of crystallization may be suitable depending the selection of host and guests. In some embodiments, the crystalline compositions are prepared from slow vapor diffusion. Slow vapor diffusion may be perform under an inert atmosphere. The crystallization may also be performed around the freezing point of water, e.g., between −10° C. and 10° C., between −8° C. and 8° C., between −6° C. and 6° C., between −4° C. and 4° C., between −2° C. and 2° C., or approximately 0° C. As demonstrated in the Examples, crystalline compositions were prepared by the slow vapor diffusion of iPr$_2$O under an Ar atmosphere at 0° C.

The crystalline compositions may be prepared from an ordered arrangement of a plurality of mixed-valence superstructure. The superstructure itself may comprise an ordered arrangement of a multiplicity of complexes. As a result, the crystalline compositions may be characterized by the ordered arrangement of the complexes or the ordered arrangement of the superstructures.

As demonstrated in the Examples, a mixed-valence complex of MV ⊂ (CBPQT)$_2$ may be prepared. The one methyl viologen, MV, is encircled by two cyclobis(paraquat-p-phenylene), CBPQT, rings. The complex bears evenly an empirical ⅔ positive charge. In other words, two positive charges are distributed statistically among a total number of 15 BIPY units assembled into three MV ⊂ (CBPQT)$_2$ complexes—that is, one electron distributed over 15 BIPY units composed of three [MV ⊂ (CBPQT)$_2$]$^{·+}$ complexes, giving an unparalleled ratio of 15:2 of BIPY/charge. The formation of this mixed-valence complex as well as its unusual ratio of BIPY/charge have been confirmed by single-crystal X-ray diffraction (XRD) which affords an empirical formula of [MV ⊂ (CBPQT)$_2$]$_3$·(PF$_6$)$_2$ for the body-centered cubic superstructure. The unprecedented nature of electron delocalization in the bulk sample has been confirmed by solid-state electron paramagnetic resonance (EPR) spectroscopy. Quantum chemistry calculations support the existence of mixed-valence state in the solid-state superstructure.

Although the ability of the neutral CBPQT$^0$ to act as a π-electron-rich host for π-electron-poor guests has been investigated, the nature of its molecular recognition towards neutral guests, such as MV$^0$, was unknown. In order to gain more insight into the binding properties of CBPQT$^0$, we investigated the reduction of an equimolar mixture of CBPQT·4PF$_6$ and MV·2PF$_6$ in MeCN solution using cobaltocene (CoCp$_2$). The UV-Vis-NIR spectrum (FIG. 1A) of this mixture before reduction exhibits no visible and NIR absorption bands and no EPR signals are observed. Upon addition of 6 equiv of CoCp$_2$ to the solution of this mixture, a new band appears at $_{max}$=367 nm with a shoulder at $_{max}$=392 nm, observations which are in line with the spectra reported[16-17] for neutral CBPQT$^0$ and MV$^0$, indicating the generation of both these neutral forms. We observed, however, a very weak broad NIR absorption band at $_{max}$=~1178 nm, which is not really noticeable until it is magnified 20-fold. This characteristic NIR absorption band, which derives from charge-resonance transitions, can be ascribed to the formation of complexes between the fully reduced BIPY$^0$ units and trace of the incompletely reduced BIPY$^{•+}$ radical cations. Consistent with the appearance of the NIR absorption band, a non-negligible weak EPR signal is also evident for the reduced solution sample, an observation which confirms the presence of radical species. The existence of both weak NIR absorption band and EPR signal indicates that, although most of this mixture is reduced to CBPQT$^0$ and MV$^0$, trace amount of BIPY units in CBPQT or MV still remain as radical cationic BIPY$^{•+}$ units which associate with its neutral counterpart BIPY$^0$ units. As a result, mixed-valence complexes are formed.

Figure 2A:
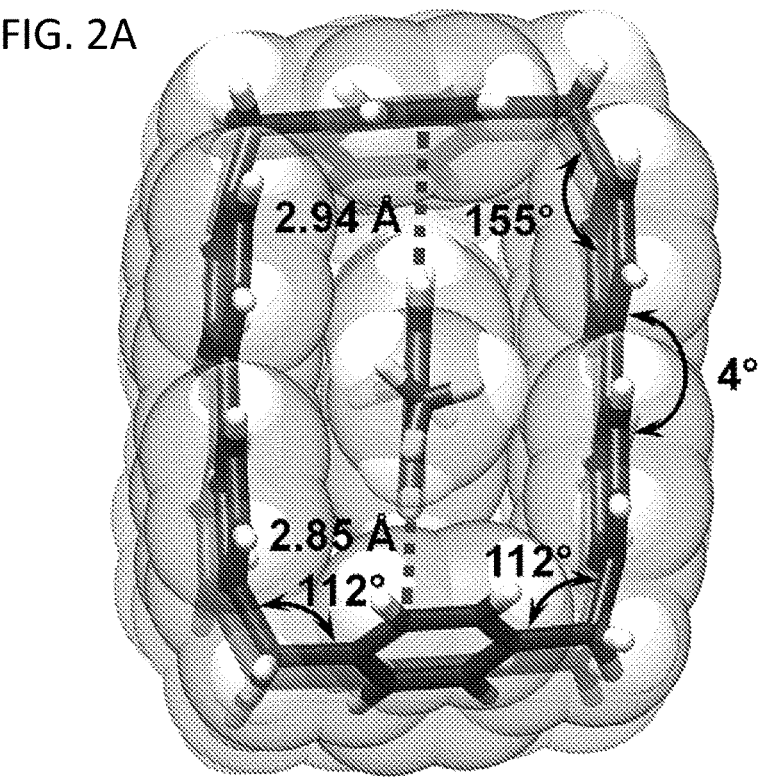
FIGS. 2A-2C show the crystal structure of $MV \subset (CBPQT)_2$.
Figure 2C:
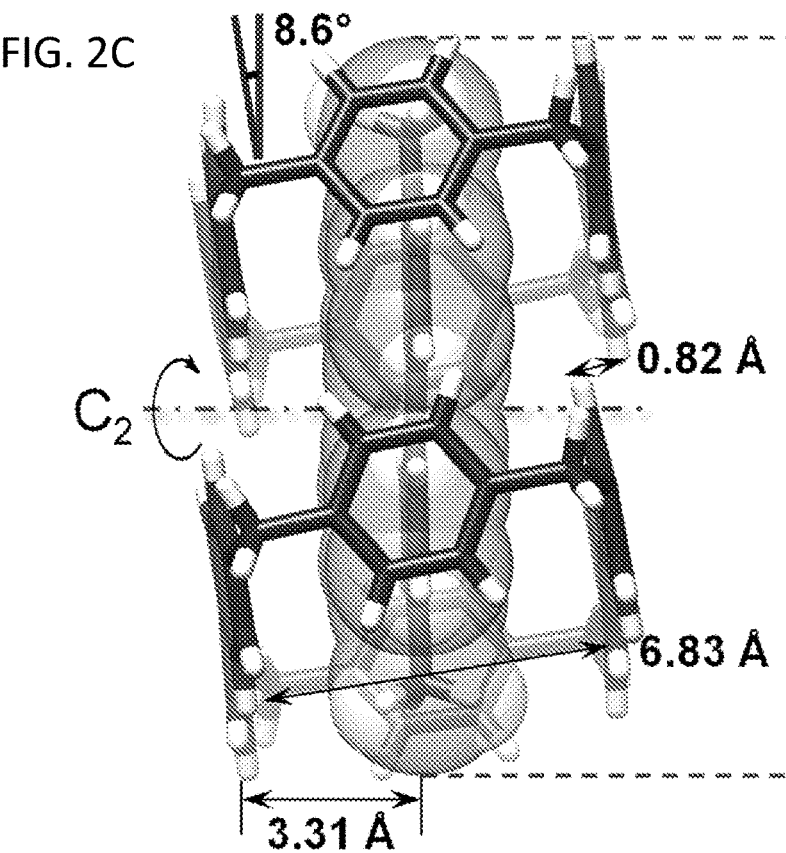
Figure 2C:
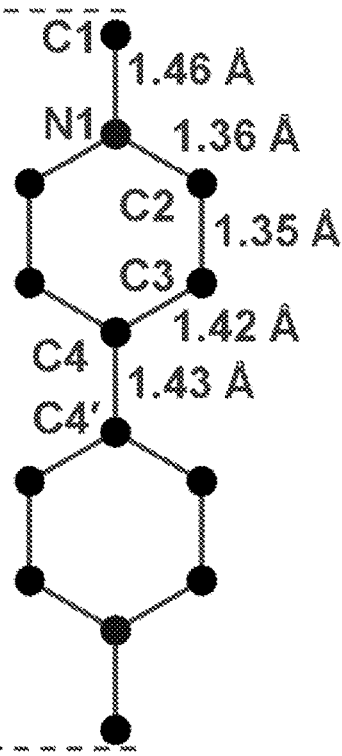
Figure 2B:
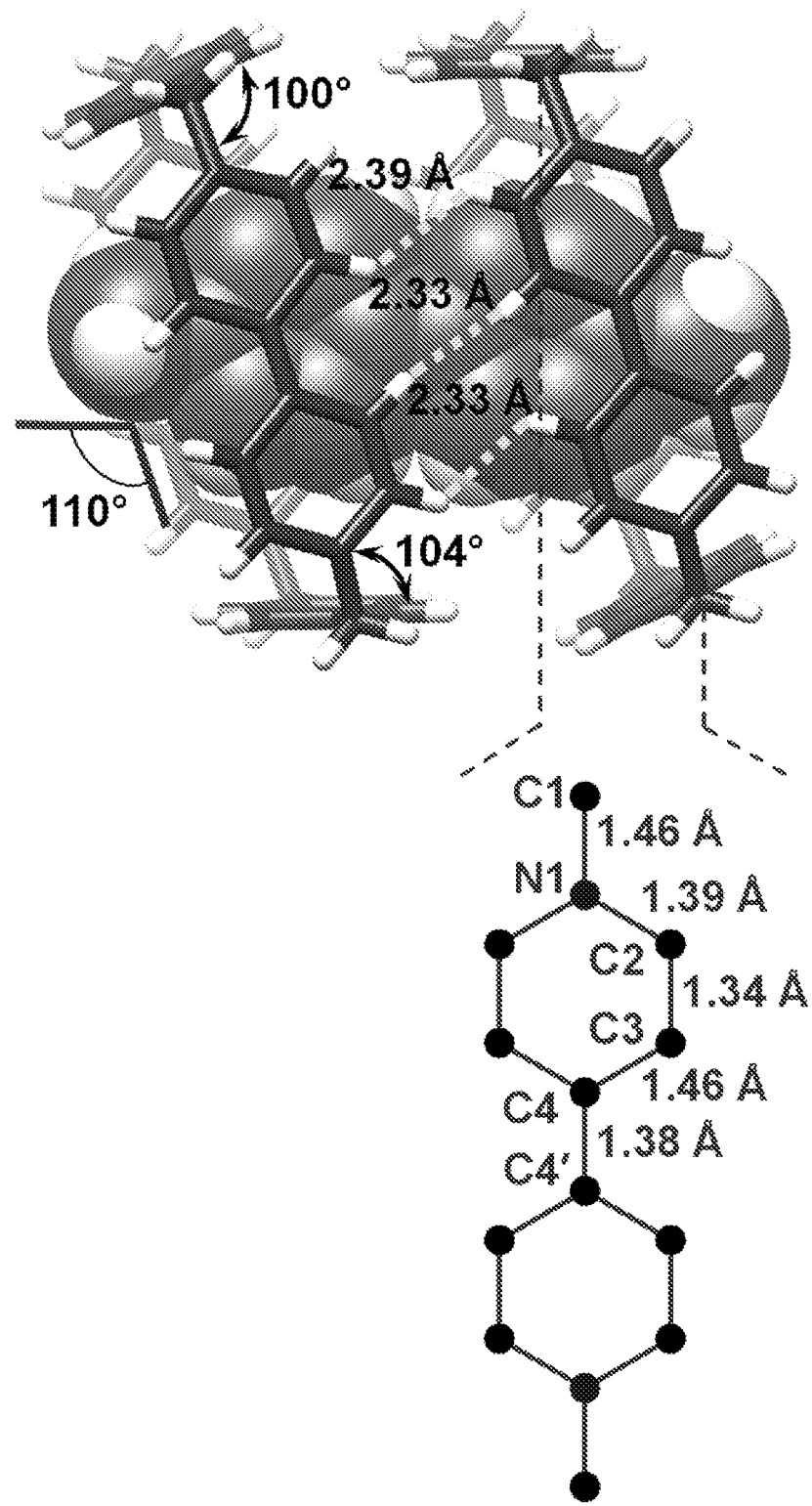

We assessed the formation of complexes in the extreme case of a mixed-valence system. Despite the rapid disproportionation of BIPY$^{•+}$ radical cations, we obtained black single crystals suitable for X-ray crystallography from a solution in MeCN/CH$_2$Cl$_2$ of an equimolar mixture of CBPQT·4PF$_6$ and MV·2PF$_6$ reduced with 6 equiv of CoCp$_2$, followed by slow vapor diffusion of iPr$_2$O under an Ar atmosphere at 0° C. The resulting black crystals are strikingly different from the red crystals of CBPQT$^0$ and MV$^0$. Single-crystal XRD analysis (FIGS. 2A-2C) shows that the superstructure is composed of a unique 2:1 host-guest inclusion complex MV⊂(CBPQT)$_2$—namely, a MV entity embraced by two CBPQT rings with a C$_2$ axis passing perpendicularly (FIG. 2C) through the center of the MV plane. Two isostructural CBPQT rings—adopting a slightly conical shape with two angles between the ring plane and two p-xylene planes of 100 and 104°—are held (FIG. 2B) together head-to-head by six [H . . . H] contacts ranging from 2.33 to 2.39 Å. The "corner" angles of CBPQT are 112°, a value which is comparable with the 113° found in the neutral CBPQT$^0$. The mean distance between two BIPY planes of the CBPQT rings is 6.83 Å, similar to the value reported[16] for the neutral CBPQT$^0$. The MV entity is encapsulated through [π . . . π] interactions of 3.31 Å between MV and two CBPQT rings as well as by four [C—H . . . π] interactions ranging from 2.85 to 2.94 Å with a dihedral angle between MV and CBPQT of 70°. Somewhat unexpectedly, the positive charge carried by this complex is observed to be a non-integer less than one—namely, [MV⊂(CBPQT)$_2$]$^{2/3+}$—on the basis of the average number of PF$_6$-anions associated with each complex, an observation which indicates that statistically every two positive charges are distributed over three MV⊂(CBPQT)$_2$ complexes which are comprised of a total number of 15 BIPY units. In other words, one electron is distributed over 15 BIPY units composed of three [MV⊂(CBPQT)$_2$]$^+$ complexes. This [MV⊂(CBPQT)$_2$]$^{2/3+}$ complex is unprecedented on account of the fact that there are no examples of (i) one aromatic guest encircled simultaneously by two host rings and (ii) a host-guest complex bearing charges more than zero but less than one.

Figure 3:
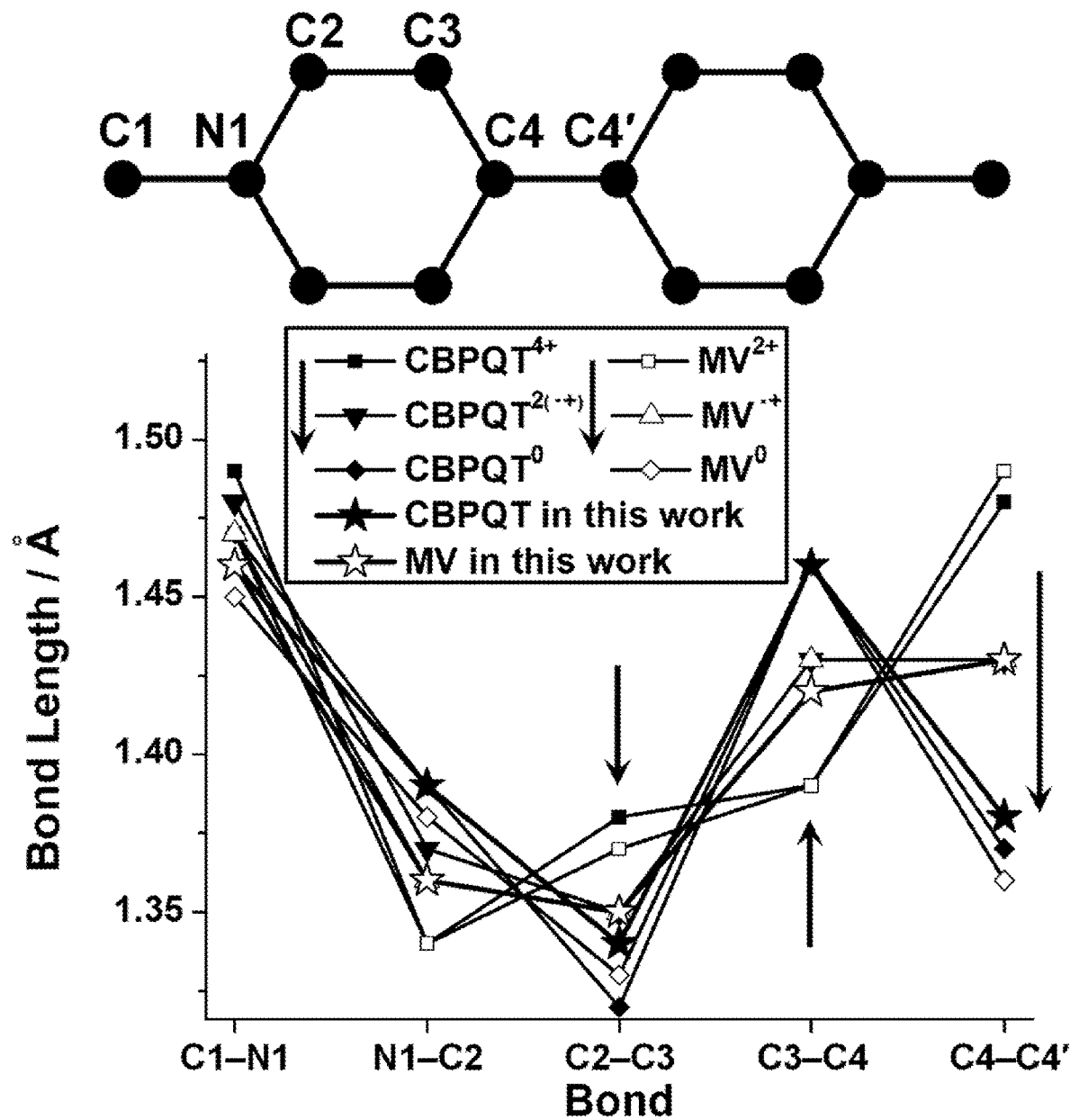
FIG. 3 compares bond lengths of the BIPY units in MV and CBPQT for a $MV \subset (CBPQT)_2$ complex with the BIPY units in $CBPQT^{4+}$, $CBPQT^{2(\cdot+)}$, and $CBPQT^0$ as well as $MV^{2+}$, $MV^{\cdot+}$, and $MV^0$. Arrows indicate the changes of bond lengths of BIPY units from oxidized to reduced states.

Despite the fact that torsional angles associated with the BIPY units change upon guest complexation, the change in the bond lengths can be used to establish[16,18-19] the oxidation states of BIPY units. In order to clarify the oxidation states of each BIPY unit of the [MV⊂(CBPQT)$_2$]$^{2/3+}$ complex, we compared the bond lengths of two classes of BIPY units in this complex with those for BIPY units reportedly[16,20] present in CBPQT$^{4+}$, CBPQT$^{2(•+)}$, and CBPQT$^0$ as well as MV$^{2+}$, MV$^{•+}$, and MV$^0$. We were able to identify (FIG. 3) a clear trend in the lengths of the bonds in BIPY units at different oxidation states—that is, upon reducing the BIPY units from the 2+ to the 0 state, the lengths of bonds C2-C3, C3-C4, C4-C4' go from long to short, from short to long, and from long to short, respectively. In particular, the bond length for C4-C4' undergoes a distinct change from ~1.49 Å (2+), to ~1.43 Å (·+), to ~1.37 Å (0), in line with the nature of bond C4-C4' changing from a single bond, a radical-delocalized bond, to a double bond. On the basis of this regularity, we found that the bond lengths of the BIPY units for the CBPQT rings in MV⊂(CBPQT)$_2$ match well with those reported for the BIPY units of CBPQT$^0$ and MV$^0$, indicating that the CBPQT ring in MV⊂(CBPQT)$_2$ is in its neutral CBPQT$^0$ state. On the other hand, the bond lengths for MV in MV⊂(CBPQT)$_2$ are comparable with those of the BIPY$^{•+}$ units in CBPQT$^{2(•+)}$ and MV$^{•+}$, observations which suggest the radical cationic MV$^{•+}$ state of MV. The results of the analysis of bond lengths indicate that most of MV⊂(CBPQT)$_2$ complexes are likely in their mixed-valence state MV$^{•+}$⊂(CBPQT$^0$)$_2$ on account of the empirical formula of [MV⊂(CBPQT)$_2$]$^{2/3+}$ of the complex.

Figure 4A:
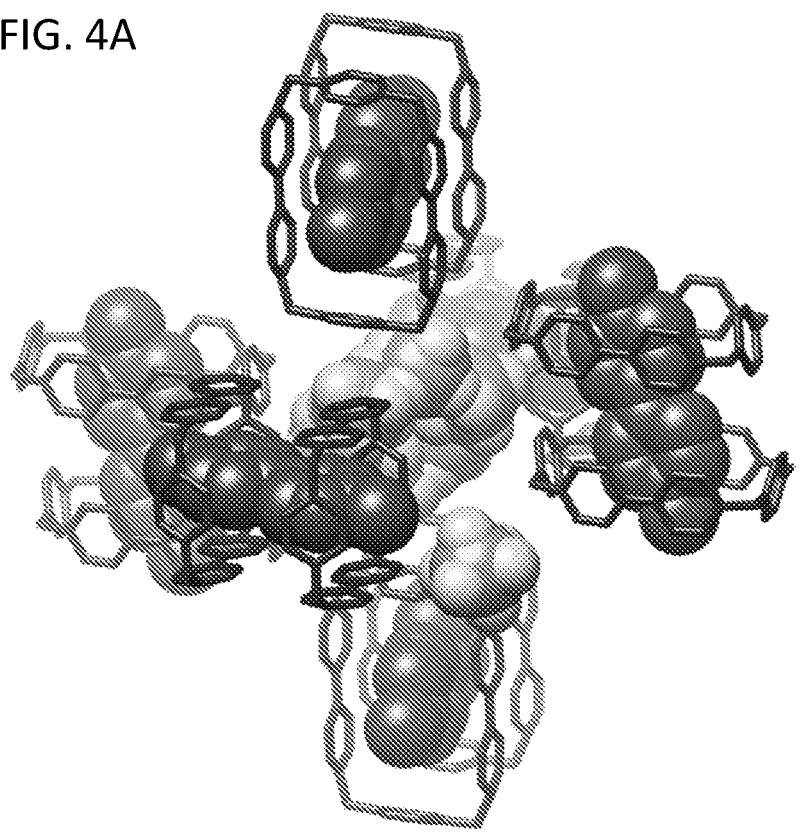
FIGS. 4A-4H shows the crystal superstructure of $[MV \subset (CBPQT)_2]_3 \cdot (PF_6)_2$.
Figure 4B:
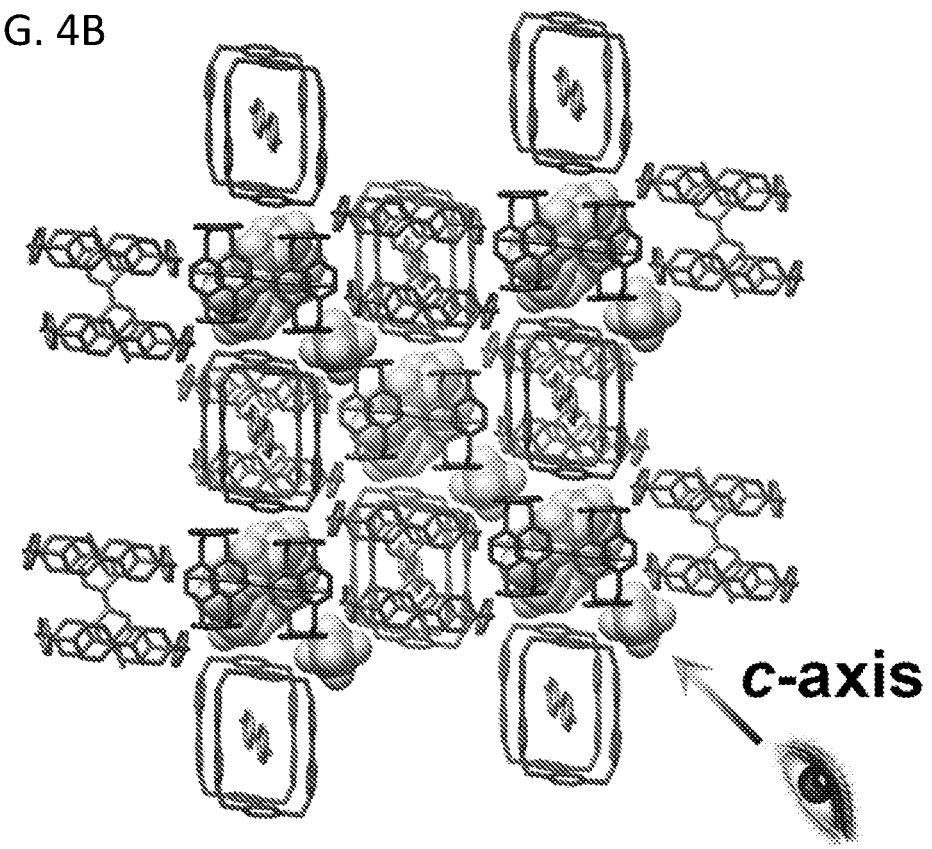
Figures 4C, 4D:
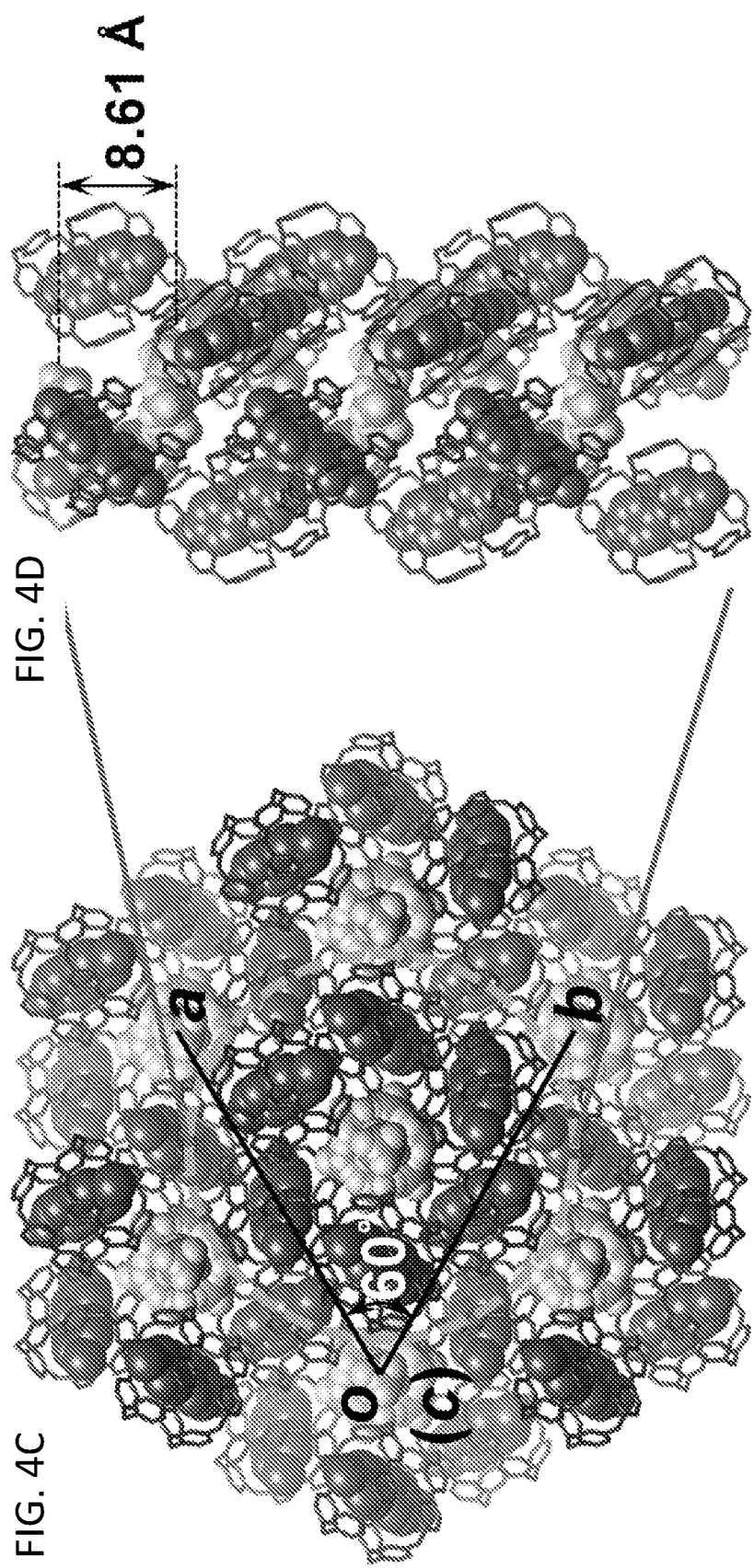
Figure 4E:
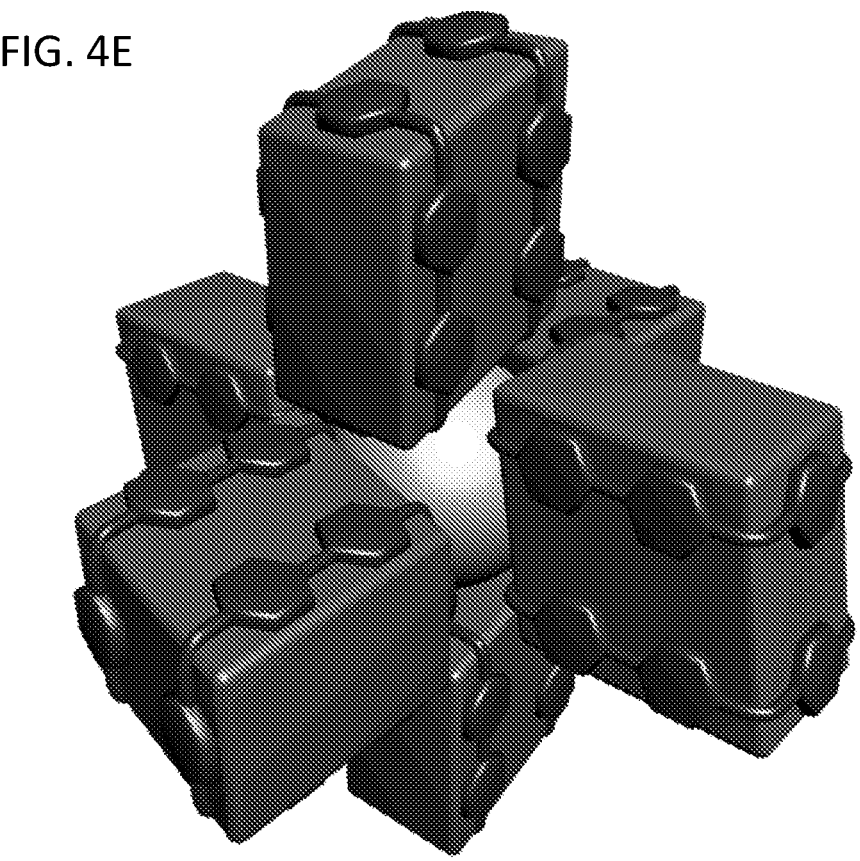
Figure 4F:
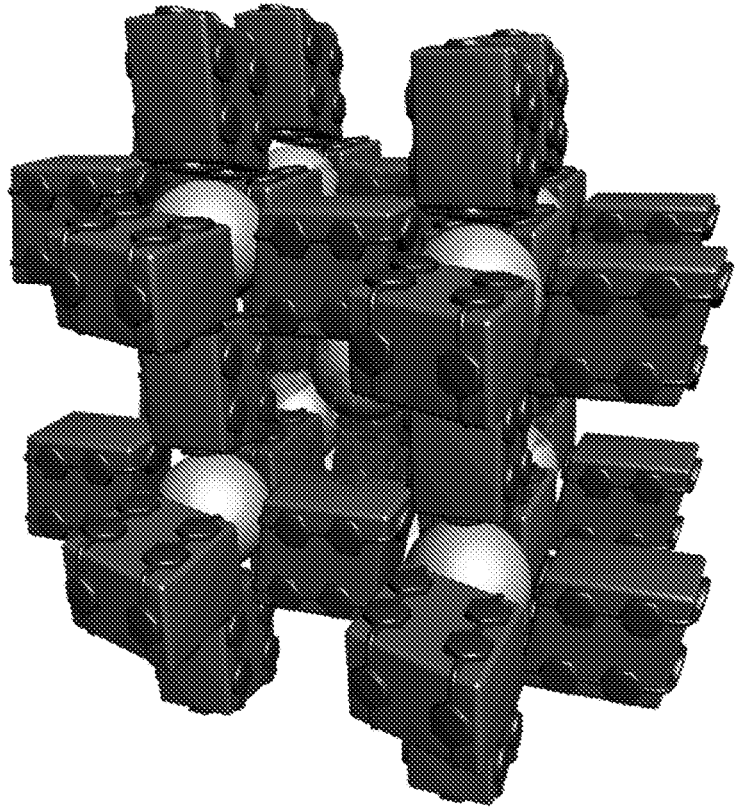
Figure 4G:
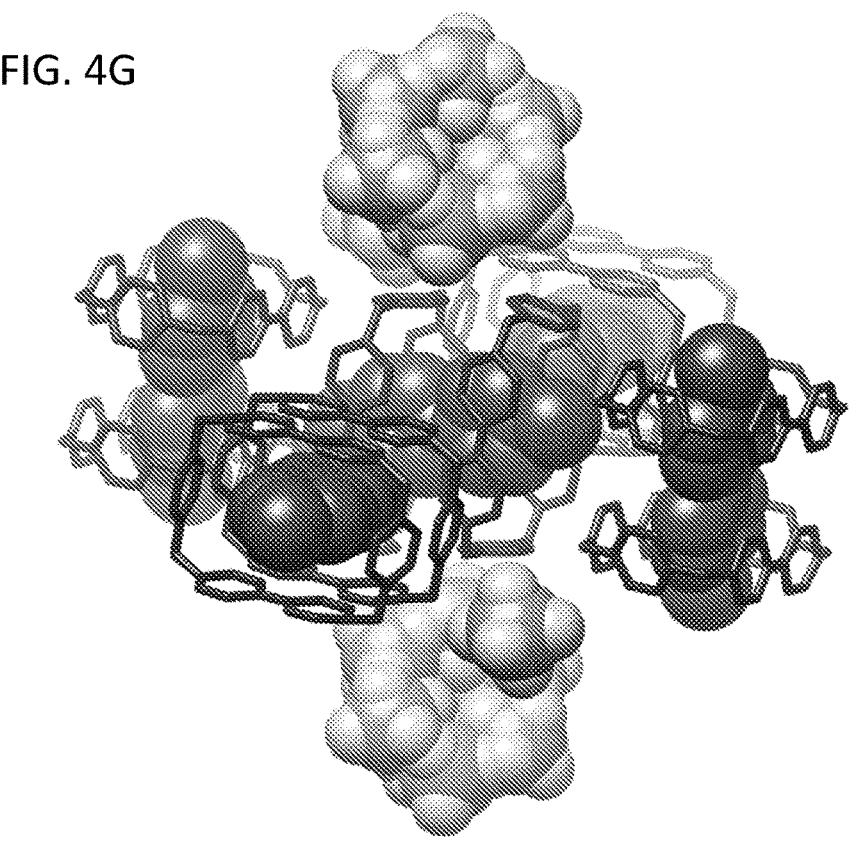
Figure 4H:
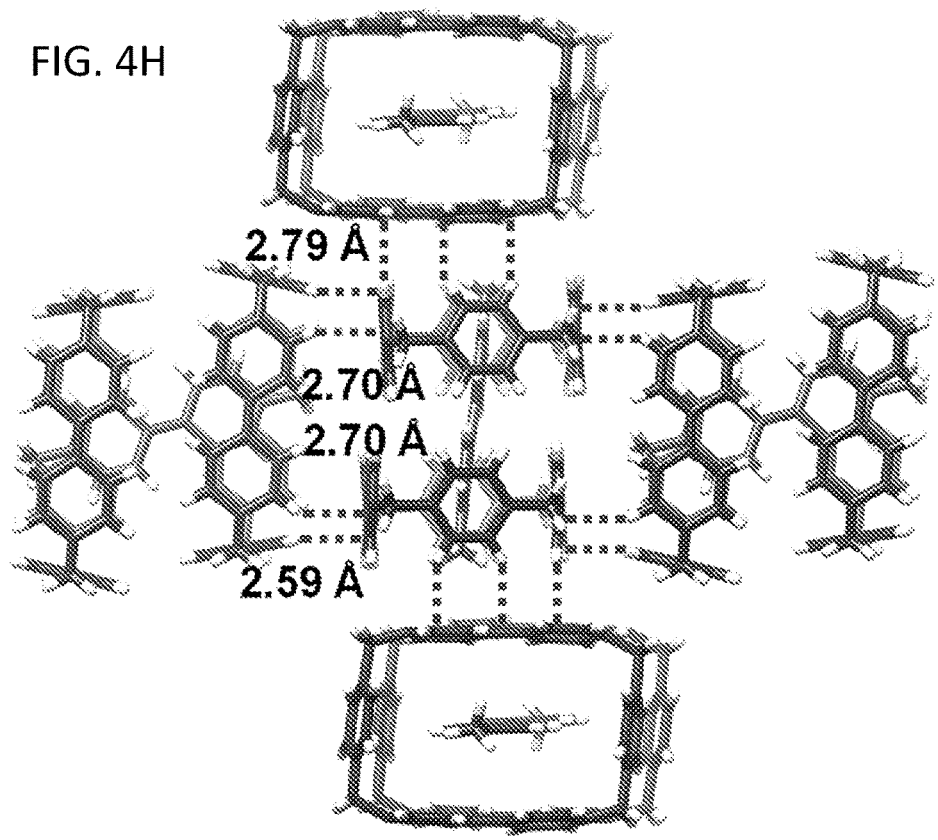
Figure 4J:
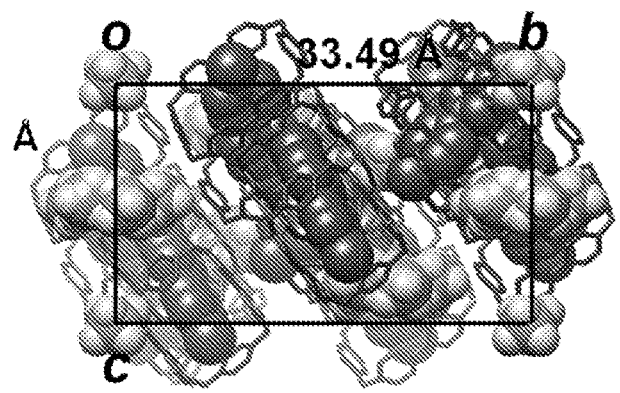

The X-ray crystal superstructure reveals that the [MV⊂(CBPQT)$_2$]$_3$·(PF$_6$)$_2$ repeating motifs adopt (FIG. 4B and FIG. 4F) an approximately body-centered cubic packing arrangement, wherein (i) anion pairs represent the vertices and the center of the cube and (ii) each MV⊂(CBPQT)$_2$ unit is linked with two anions through its two outward-pointing para-xylylene faces. For every two PF$_6^-$ anions, one of them is disordered (FIGS. 4I-4K) about a six-fold crystallographic c-axis. These counter ions are surrounded by the para-xylene planes of six MV⊂(CBPQT)$_2$ units to form (FIG. 4A and FIG. 4E) an octahedron wherein six MV⊂(CBPQT)$_2$ units occupy the vertices. The counter ions also serve as shared linkers in connecting these octahedrons together in a three-dimensional array which extends throughout the whole crystal. As a result, every octahedron has the empirical formula of [MV⊂(CBPQT)$_2$]$_3$·(PF$_6$)$_2$.

Figure 4L:
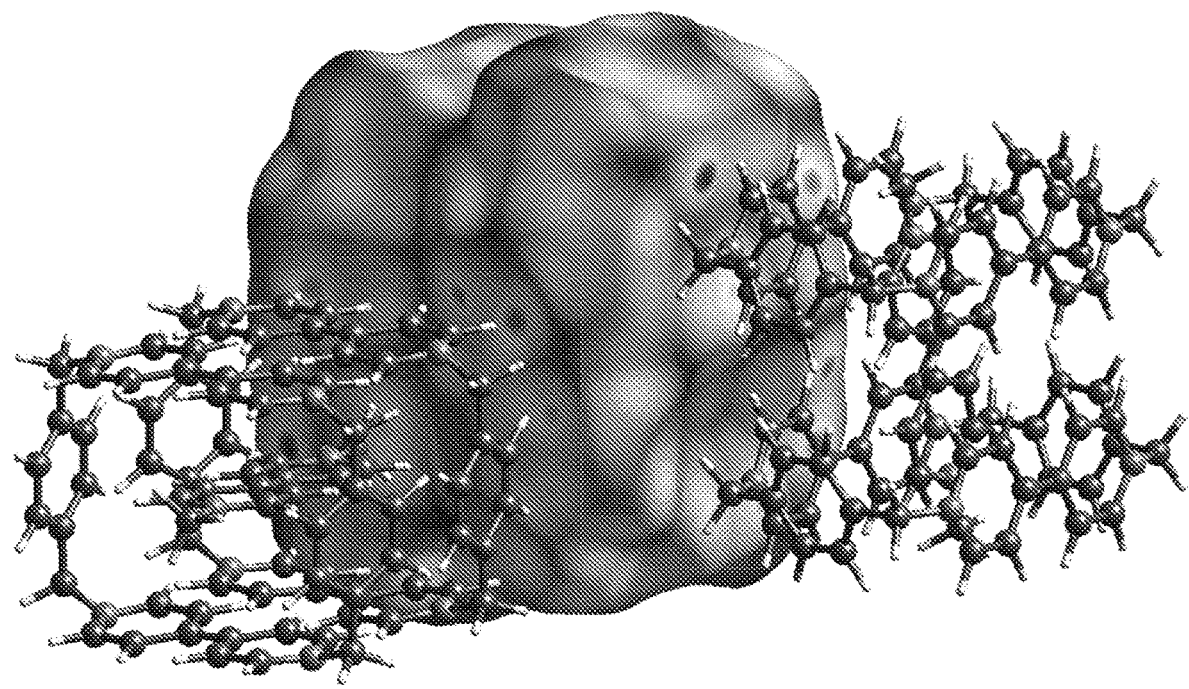
FIG. 4L shows a Hirshfeld surface plot of $MV \subset (CBPQT)_2$. Dark spots in the $d_{norm}$ surface mapping are the result of [C—H . . . π] interactions between BIPY planes and the H atoms on CBPQT rings of three adjacent but orthogonally oriented complexes. On account of the $C_2$ symmetry of the $MV \subset (CBPQT)_2$ complex, another 10 two-fold symmetry-related complementary [C—H . . . π] interactions exist between the opposite BIPY planes and the H atoms on the opposite CBPQT rings of each complex. The reciprocal [C—H . . . π]/[π . . . H—C] interactions are the most significant inter-complex interactions which contribute 79.8% to the Hirshfeld surface.
Figure 5:
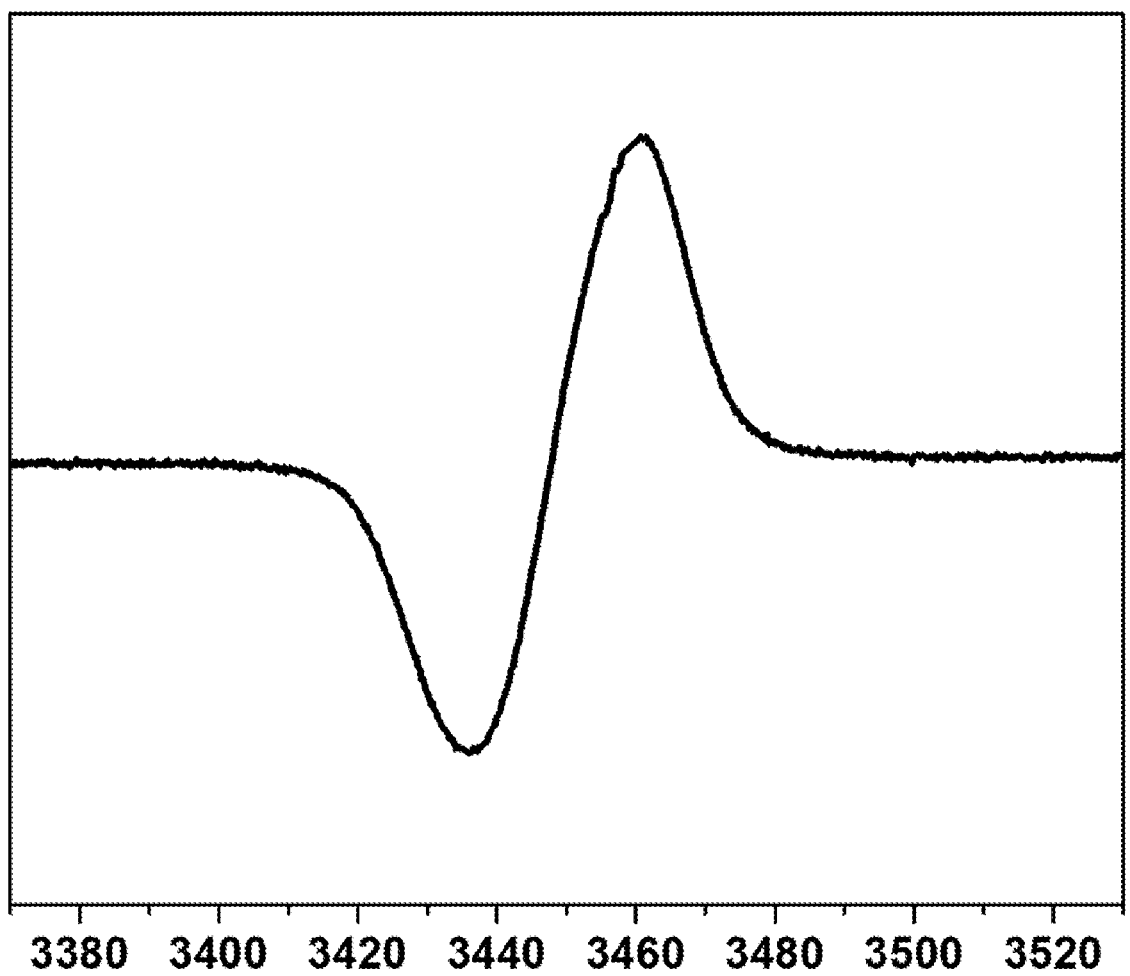
FIG. 5 shows a solid-state continuous-wave EPR spectrum of single crystals of $[MV \subset (CBPQT)_2]_3 \cdot (PF_6)_2$, demonstrating the presence of free radicals in the solid-state superstructure.

As viewed along the crystallographic c-axis (the diagonal of the cube, FIG. 4B), hexagonal channels—which are filled (FIG. 4D) up with PF$_6^-$ anions spaced 8.61 Å apart from each other and penetrate through every octahedron—can be observed to pack (FIG. 4C and FIGS. 4I-4K)) into hexagonal arrangement. In the superstructure, every MV⊂(CBPQT)$_2$ unit is encircled (FIG. 4G) by four adjacent MV⊂(CBPQT)$_2$ in the equatorial plane and two pairs of PF$_6^-$ anions at the two vertices generating an octahedron. Since every complex has three types of facets—namely, para-xylylene planes, BIPY planes, and CBPQT ring planes—in which the para-xylylene planes interact with PF$_6^-$ anions, every MV⊂(CBPQT)$_2$ links (FIG. 4B, FIG. 4H, and FIG. 4L) with four adjacent but orthogonally oriented MV⊂(CBPQT)$_2$ units by means of 20 complementary [C—H . . . π] interactions ranging from 2.59-2.79 Å between the BIPY planes and the H atoms on the CBPQT rings, assembling (FIG. 4G) into an extended body-centered cubic framework with PF$_6^-$ pairs as vertices and center of each cube. Hirshfeld surface analysis confirms[21] (FIG. 4L) that the reciprocal [C—H . . . π]/[π . . . H—C] interactions, which contribute 79.8%, are the most significant interactions between MV⊂(CBPQT)$_2$ units. This extended superstructure can be a result of the even distribution of the positive charges throughout the whole crystal. The existence of the unpaired electrons in the mixed-valence crystals was also confirmed by solid-state EPR spectroscopy. An isotropic EPR signal, which was obtained (FIG. 5) on a crystal sample, had a g-factor similar to those reported for mixed-valence BIPY$^{·+}$-containing solid-state samples[16], an observation which indicates the presence of free radicals in the solid-state superstructure. On account of the fact that no single MV⊂(CBPQT)$_2$ unit bears statistically one full positive charge on the basis of the empirical formula of [MV⊂(CBPQT)$_2$]$_3$·(PF$_6$)$_2$, we believe that the unpaired electron delocalizes at least over five viologen units inside the MV⊂(CBPQT)$_2$ complex.

Quantum chemistry calculations were carried out to analyze the charge distribution inside and between MV⊂(CBPQT)$_2$ in solid state. The optimized unit cell involves three MV⊂(CBPQT)$_2$ complexes (a, b and c) and two PF$_6^-$ anions. Mulliken charge and spin population analysis of each MV⊂(CBPQT)$_2$ and MV shows (Table 2) that two positive charges are not evenly distributed on three MV⊂(CBPQT)$_2$ but localized on two MV$^{·+}$⊂(CBPQT$^0$)$_2$ with one MV$^0$⊂(CBPQT$^0$)$_2$ in neutral. The uneven distribution of positive charge attracts PF$_6^-$ anions, making one of them drift away from the 3-fold axis to the position that is closer to two MV$^{·+}$⊂(CBPQT$^0$)$_2$. Such an effect is in line with the observation from X-ray crystallography which shows that one of the PF$_6^-$ pair does not have one single position with equal distances between MV⊂(CBPQT)$_2$, but disorders over six symmetry-equivalent positions with ⅙ occupancy at each.

We have demonstrated that two host rings are able to encapsulate cooperatively one aromatic guest to form a mixed-valence 2:1 host-guest inclusion complex such as MV⊂(CBPQT)$_2$. Single-crystal XRD analysis indicates that every three inclusion complexes share statistically two positive charges to give an extended body-centered cubic superstructure. The fact that every inclusion complex bears an empirical charge of ⅔+ suggests the distribution of every two positive charges over 15 BIPY units composing three complexed, giving an unprecedented ratio of 15:2 of BIPY/charge. In other words, one electron is distributed over 15 BIPY units which composed of three 2:1 host-guest inclusion complexes. Quantum chemistry calculations confirm the nature of the mixed-valence state of the solid-state superstructure. This research highlights host-guest strategies for achieving long-range charge delocalization in solid-state devices by constructing host-guest complexes with precisely adjustable redox states.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

1. General Methods

All reagents were purchased from commercial suppliers and used without further purification. Methyl viologen (paraquat) bis(hexafluorophosphate) (MV·2PF$_6$) and cyclobis(paraquat-p-phenylene) tetrakis(hexafluorophosphate) (CBPQT·4PF$_6$) were prepared[22] according to literature procedures. Bis(cyclopentadienyl)cobalt(II) (cobaltocene, CoCp$_2$) was purchased from Sigma-Aldrich and stored in an Ar-filled glovebox. Prior to experiments, CoCp$_2$ was assayed in dried and degassed MeCN using a colorimetric method. All experiments were performed in MeCN solutions, previously degassed, in a glovebox under an Ar atmosphere. Thin layer chromatography (TLC) was performed on silica gel 60 F254 (E. Merck). Column chromatography was carried out on silica gel 60F (Merck 9385, 0.040-0.063 mm). UV/Vis Spectra were recorded at room temperature on a Shimadzu UV-3600 spectrophotometer in a quartz cell with an optical path-length of 2 mm containing the solution of interest. Samples were prepared immediately prior to use and the solutions were sealed under Ar with Teflon stoppers. Experimental error: absorption maxima, ±1 nm. Electron paramagnetic resonance (EPR) measurements at X-band (9.5 GHz) were performed with a Bruker Elexsys E580, equipped with a variable Q dielectric resonator (ER-4118X-MD5-W1). All samples were prepared in an Ar-filled atmosphere. Samples were loaded into quartz 1.4 mm tubes and sealed with a clear ridged UV doming epoxy (Illuma-Bond 60-7160RCL) and used immediately after preparation. Steady-state solution CW EPR spectra were collected with a 0.25 G modulation amplitude 2.56 ms time constant, and 10.24 ms conversion time, averaging 100 sweeps 50 G wide, centered around 2465 G. Steady-state solid continuous-wave EPR spectra were measured with the same parameters with a modulation amplitude of 0.05 G on a sample of several crystals of complex $[MV \subset (CBPQT)_2]_3 \cdot (PF_6)_2$—which was confirmed by single-crystal X-ray diffraction—in a quartz 1.4 mm tube in Ar. Single-crystal data was measured on a Bruker Kappa APEX2 CCD diffractometer using Cu—Kα radiation. Data collection and structure refinement details can be found in the CIF file. CCDC 985866 contains the supplementary crystallographic data for this paper.

2. Solution-State Characterization of the Equimolar Mixture of CBPQT and MV 2.1. UV-Vis-NIR Spectroscopy A solution of the reduced equimolar mixture of CBPQT and MV in MeCN was prepared by the chemical reduction of a fully oxidize equimolar mixture of CBPQT·4PF$_6$ and MV·2PF$_6$ using 6.0 equiv of CoCp$_2$. The UV-Vis-NIR spectra were recorded on solutions with 1:0 and 1:6 molar ratios of the 1:1 mixture CBPQT·4PF$_6$/MV·2PF$_6$:CoCp$_2$ in a final volume of 1.00 mL by using CBPQT·4PF$_6$/MV·2PF$_6$ (80 μM) and CoCp$_2$ (1.7 mM) solutions in MeCN. UV-Vis-NIR Spectra of solutions were recorded in the wavelength window of 275-2200 nm using a 2-mm quartz cuvette.

2.2. EPR Spectroscopy

Samples for EPR investigations were prepared as described for the carrying out of the UV-Vis spectroscopy with the exception that the concentration of the stock solution of the equimolar mixture of CBPQT·4PF$_6$ and MV·2PF$_6$ was maintained at 250 μM. The EPR spectra of CBPQT·4PF$_6$/MV·2PF$_6$ and its reduced product were recorded at 298 K after the chemical reduction with 6 equiv of CoCp$_2$.

3. Crystallographic Characterization 3.1. Method

Single crystals of $[MV \subset (CBPQT)_2]_3 \cdot (PF_6)_2$ were grown under inert (Ar) atmosphere at 0° C. by slow vapor diffusion of iPr$_2$O into a MeCN/CH$_2$Cl$_2$ solution containing an equimolar mixture of CBPQT and MV prepared by the chemical reduction of an equimolar mixture of CBPQT·4PF$_6$ and MV·2PF$_6$ using 6.0 equiv of CoCp$_2$. A black single crystal suitable for crystallographic analysis was selected and mounted in inert oil and transferred to the cold gas stream of a Bruker Kappa APEX2 CCD area detector equipped with a Cu—Kα microsource with MX optics. SADABS-2008/1 (Bruker, 2008) was used for absorption correction. wR$_2$(int) was 0.0748 before and 0.0585 after correction. The ratio of minimum to maximum transmission is 0.8704. The λ/2 correction factor is 0.0015.

3.2. Crystal Structure Determination of $[MV \subset (CBPQT)_2]_3 \cdot (PF_6)_2$ Crystal Data of $[MV \subset (CBPQT)_2]_3 \cdot (PF_6)_2$: M=3972.68, trigonal, space group R$\bar{3}$ (no. 148), a=33.494 (3), c=17.2240 (17) Å, U=16734 (4) c$^3$, T=100.01 K, Z=3, μ(Cu—Kα)= 0.786 mm$^{-1}$. A total of 32335 reflections were collected, of which 5902 (R$_{int}$=0.0414) were unique and used in all calculations. The final wR (F$_2$) was 0.1809 (all data).

3.3. Refinement Details

One PF$_6^-$ counteranion is disordered about a six-fold crystallographic axis. Displacement parameters of the P and F atoms were refined with rigid bond (DELU) and similarity (SIMU) restraints. P—F and F—F distances were refined with SADI restraints to keep the octahedral geometry reasonable.

TABLE 1

Crystal Data and Structure Refinement for $[MV \subset (CBPQT)_2]_3 \cdot (PF_6)_2$

| | |
|---|---|
| Empirical Formula | $[MV \subset (CBPQT)_2]_3 \cdot (PF_6)_2$ |
| Formula Weight | 3972.68 |
| T/K | 100.01 |
| Crystal System | Trigonal |
| Space Group | R$\bar{3}$ |
| a, b, c/Å | 33.494 (3), 33.494 (3), 17.2240 (17) |
| α, β, γ/° | 90, 90, 120 |
| V/Å$^3$ | 16734 (4) |
| Z | 3 |
| ρ$_{calc}$/mg mm$^{-3}$ | 1.256 |
| μ/mm$^{-1}$ | 0.786 |
| F(000) | 6678 |
| Crystal Size/mm$^3$ | 0.161 × 0.109 × 0.086 |
| 2θ Range for Data Collection | 9.146 to 124.7° |
| Index Ranges | −38 ≤ h ≤ 38, −38 ≤ k ≤ 38, −13 ≤ l ≤ 19 |
| Reflections Collected | 32335 |
| Independent Reflections | 5902 [R$_{int}$ = 0.0414] |
| Data/Restraints/Parameters | 5902/189/527 |
| Goodness-of-Fit on F$^2$ | 1.096 |
| Final R Indexes [I > 2σ (I)] | R$_1$ = 0.0534, wR$_2$ = 0.1722 |
| Final R Indexes [all data] | R$_1$ = 0.0600, wR$_2$ = 0.1809 |
| Largest diff. peak/hole/e Å$^{-3}$ | 0.631/−0.321 |

4. DFT Calculations

All the periodic calculations were carried out with CRYSTAL14[24] at the level of M06-HF/6-31G*. In order to prepare the initial geometry, the Rsymmetry was removed from the single-crystal XRD structure and among six symmetry-equivalent positions of PF$_6^-$ anions, one was selected. The broken symmetry initial guess was provided so electrons with different spin were allowed to populate in different orbitals.

TABLE 2

The Mulliken Charge and Spin Population of Each Molecule in the Periodic Calculation

| Complex | Fragment | Charge | Spin |
|---|---|---|---|
| a | MV ⊂ (CBPQT)$_2$ | 0.74 | −1.00 |
| | MV | 0.78 | −0.98 |
| b | MV ⊂ (CBPQT)$_2$ | 0.73 | 1.00 |
| | MV | 0.79 | 0.98 |
| c | MV ⊂ (CBPQT)$_2$ | −0.09 | −0.00 |
| | MV | −0.06 | −0.00 |

REFERENCES (1) Winkler, J. R.; Gray, H. B. *J. Am. Chem. Soc.* 2014, 136, 2930.

(2) McDermott, G.; Prince, S. M.; Freer, A. A.; Hawthornthwaite-Lawless, A. M.; Papiz, M. Z.; Cogdell, R. J.; Isaacs, N. W. *Nature* 1995, 374, 517.

(3) Zhu, W.; Zheng, R.; Fu, X.; Fu, H.; Shi, Q.; Zhen, Y.; Dong, H.; Hu, W. Angew. Chem. Int. Ed. 2015, 54, 6785.

(4) Murase, T.; Otsuka, K.; Fujita, M. *J. Am. Chem. Soc.* 2010, 132, 7864.

(5) Leblanc, N.; Mercier, N.; Toma, O.; Kassiba, A. H.; Zorina, L.; Auban-Senzier, P.; Pasquier, C. *Chem. Commun.* 2013, 49, 10272.

(6) Hankache, J.; Wenger, O. S. *Chem. Rev.* 2011, 111, 5138.

(7) Yoshizawa, M.; Kumazawa, K.; Fujita, M. *J. Am. Chem. Soc.* 2005, 127, 13456.

(8) Lindeman, S. V.; Rosokha, S. V.; Sun, D.; Kochi, J. K. *J. Am. Chem. Soc.* 2002, 124, 843.

(9) Berville, M.; Karmazin, L.; Wytko, J. A.; Weiss, *J. Chem. Commun.* 2015, 51, 15772.

(10) Ko, Y. H.; Kim, E.; Hwang, I.; Kim, K. *Chem. Commun.* 2007, 1305.

(11) Odell, B.; Reddington, M. V.; Slawin, A. M. Z.; Spencer, N.; Stoddart, J. F.; Williams, D. J. *Angew. Chem. Int. Ed.* 1988, 27, 1547.

(12) Trabolsi, A.; Khashab, N.; Fahrenbach, A. C.; Friedman, D. C.; Colvin, M. T.; Coti, K. K.; Benitez, D.; Tkatchouk, E.; Olsen, J.-C.; Belowich, M. E.; Carmielli, R.; Khatib, H. A.; Goddard, W. A., III; Wasielewski, M. R.; Stoddart, J. F. *Nat. Chem.* 2010, 2, 42.

(13) Geraskina, M. R.; Dutton, A. S.; Juetten, M. J.; Wood, S. A.; Winter, A. H. *Angew. Chem. Int. Ed.* 2017, 56, 9435.

(14) Li, H.; Zhu, Z.; Fahrenbach, A. C.; Savoie, B. M.; Ke, C.; Barnes, J. C.; Lei, J.; Zhao, Y.-L.; Lilley, L. M.; Marks, T. J.; Ratner, M. A.; Stoddart, J. F. *J. Am. Chem. Soc.* 2013, 135, 456.

(15) Sun, J.; Liu, Z.; Liu, W.-G.; Wu, Y.; Wang, Y.; Barnes, J. C.; Hermann, K. R.; Goddard, W. A., III; Wasielewski, M. R.; Stoddart, J. F. *J. Am. Chem. Soc.* 2017, 139, 12704.

(16) Frasconi, M.; Fernando, I. R.; Wu, Y.; Liu, Z.; Liu, W.-G.; Dyar, S. M.; Barin, G.; Wasielewski, M. R.; Goddard, W. A., III; Stoddart, J. F. *J. Am. Chem. Soc.* 2015, 137, 11057.

(17) Bockman, T. M.; Kochi, J. K. *J. Org. Chem.* 1990, 55, 4127.

(18) Porter, W. W.; Vaid, T. P.; Rheingold, A. L. *J. Am. Chem. Soc.* 2005, 127, 16559.

(19) Ivanov, M. V.; Wang, D.; Navale, T. S.; Lindeman, S. V.; Rathore, R. *Angew. Chem. Int. Ed.* 2018, 57, 2144.

(20) Fahrenbach, A. C.; Barnes, J. C.; Lanfranchi, D. A.; Li, H.; Coskun, A.; Gassensmith, J. J.; Liu, Z.; Benitez, D.; Trabolsi, A.; Goddard, W. A., III; Elhabiri, M.; Stoddart, J. F. *J. Am. Chem. Soc.* 2012, 134, 3061.

(21) Turner, M. J.; McKinnon, J. J.; Wolff, S. K.; Grimwood, D. J.; Spackman, P. R.; Jayatilaka, D.; Spackman, M. A. *CrystalExplorer17*; University of Western Australia, 2017.

(22) Ashton, P. R.; Boyd, S. E.; Brindle, A.; Langford, S. J.; Menzer, S.; Perez-Garcia, L.; Preece, J. A.; Raymo, F. M.; Spencer, N.; Stoddart, J. F.; White, A. J. P.; Williams, D. J. *New J. Chem.* 1999, 23, 587.

(23) Turner, M. J.; McKinnon, J. J.; Wolff, S. K.; Grimwood, D. J.; Spackman, P. R.; Jayatilaka, D.; Spackman, M. A. *CrystalExplorer17*; University of Western Australia, 2017.

(24) Dovesi, R.; Orlando, R.; Erba, A.; Zicovich-Wilson, C. M.; Civalleri, B.; Casassa, S.; Maschio, L.; Ferrabone, M.; De La Pierre, M.; D'Arco, P.; Noel, Y.; Causa, M.; Rerat, M.; Kirtman, B., Crystal14: A program for the ab initio investigation of crystalline solids. *Int. J. Quant. Chem.* 2014, 114, 1287.

We claim:

1. A mixed-valence host-guest inclusion complex comprising an aromatic guest encircled by two macrocycles, wherein the complex has an empirical charge greater than 0 and less than 1.

2. The complex of claim 1, wherein the aromatic guest comprises Formula I

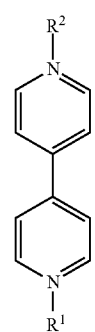

wherein $R^1$ and $R^2$ are each independently selected from alkyl, cycloalkyl, heterocycloalkyl, aryl, heteroaryl, alkenyl, alkynyl, alkyleneazido, alkylenecycloalkyl, alkyleneheterocycloalkyl, or alkylenearyl.

3. The complex of claim 2, wherein the aromatic guest comprises methyl viologen.

4. The complex of claim 1, wherein each of the two macrocycles encircling the aromatic guest comprise cyclobis(paraquat-p-phenylene).

5. The complex of claim 4, wherein the complex has an empirical formula of $[MV \subset (CBPQT)_2]^{2/3+}$.

6. A mixed-valence superstructure comprising an ordered arrangement of a multiplicity of complexes as in claim 1 and a counter anion.

7. The superstructure of claim 6, wherein the superstructure comprises an octahedral arrangement of the multiplicity of complexes.

8. The superstructure of claim 6, wherein the superstructure has an empirical formula of $[MV \subset (CBPQT)_2]_3 \cdot (PF_6)_2$.

9. A crystalline composition comprising an ordered arrangement of a plurality of superstructures as in claim 6.

10. The composition of claim 9, wherein the composition comprises a body-centered cubic arrangement of the plurality of superstructures.

11. The composition of claim 9, wherein the ordered arrangement results in channels.

12. The composition of claim 11, wherein the composition comprises the counter anion disposed within the channels.

13. The composition of claim 9, wherein the composition has an empirical formula of $[MV \subset (CBPQT)_2]_3 \cdot (PF_6)_2$.

14. The composition of claim 9, wherein the composition has a molecular packing arrangement defined by space group $R\bar{3}$.

15. The composition of claim 9, wherein the composition has a molecular packing arrangement defined by unit cell dimensions a=33.5±0.1, b=33.5±0.1, c=17.2±0.1, α=90°, β=90°, and γ=120°.

16. A method for the preparation of a mixed-valence host-guest complex, the method comprising contacting a mixture comprising an aromatic guest and a macrocycle with a reducing agent to prepare the mixed-valence host guest complex, wherein the mixed-valence host guest complex comprises an aromatic guest encircled by two macrocycles and wherein the complex has an empirical charge greater than 0 and less than 1.

17. The method for the preparation of a crystalline composition, the method comprising contacting a mixture comprising an aromatic guest and a macrocycle with a reducing agent to prepare a plurality of mixed-valence host guest complexes and crystallizing the plurality of complexes to prepare the crystalline composition, wherein the mixed-valence host guest complex comprises an aromatic guest encircled by two macrocycles, wherein the complex has an empirical charge greater than 0 and less than 1, and wherein the crystalline composition comprises an ordered arrangement of a plurality of complexes.

18. The method of claim 16, wherein the mixture is contacted with between 2 and 10 equivalents of the reducing agent and/or the mixture is a solution comprising a molar ration between 2.0:1.0 and 1.0:2.0 of aromatic guest to macrocycle.

19. The method of claim 16, wherein the complex has an empirical formula of $[MV \subset (CBPQT)_2]^{2/3+}$.

20. The method of claim 15, wherein the composition comprises a mixed-valence superstructure having an empirical formula of $[MV \subset (CBPQT)_2]_3 \cdot (PF_6)_2$.

* * * * *